(12) United States Patent
Kim et al.

(10) Patent No.: US 9,184,392 B2
(45) Date of Patent: Nov. 10, 2015

(54) POLYMER AND ORGANIC SOLAR CELL INCLUDING SAME

(71) Applicant: LG CHEM, LTD., Seoul (KR)

(72) Inventors: Jinseck Kim, Daejeon (KR); Jeong Min Choi, Daejeon (KR); Jaesoon Bae, Daejeon (KR); Jiyoung Lee, Daejeon (KR)

(73) Assignee: LG CHEM, LTD., Seoul (KR)

( * ) Notice: Subject to any disclaimer, the term of this patent is extended or adjusted under 35 U.S.C. 154(b) by 0 days.

(21) Appl. No.: 14/354,088

(22) PCT Filed: Feb. 5, 2013

(86) PCT No.: PCT/KR2013/000919
§ 371 (c)(1),
(2) Date: Apr. 24, 2014

(87) PCT Pub. No.: WO2013/119022
PCT Pub. Date: Aug. 15, 2013

(65) Prior Publication Data
US 2014/0290747 A1 Oct. 2, 2014

(30) Foreign Application Priority Data

| Feb. 6, 2012 | (KR) | 10-2012-0011980 |
| Oct. 16, 2012 | (KR) | 10-2012-0114808 |
| Feb. 4, 2013 | (KR) | 10-2013-0012261 |

(51) Int. Cl.
| C08G 75/00 | (2006.01) |
| H01L 51/00 | (2006.01) |
| C07D 417/14 | (2006.01) |
| C08G 61/12 | (2006.01) |
| H01L 51/42 | (2006.01) |

(52) U.S. Cl.
CPC .......... *H01L 51/0036* (2013.01); *C07D 417/14* (2013.01); *C08G 61/123* (2013.01); *C08G 61/124* (2013.01); *C08G 61/126* (2013.01); *H01L 51/0035* (2013.01); *H01L 51/0043* (2013.01); *C08G 2261/1412* (2013.01); *C08G 2261/1414* (2013.01); *C08G 2261/1424* (2013.01); *C08G 2261/3223* (2013.01); *C08G 2261/3241* (2013.01); *C08G 2261/3243* (2013.01); *C08G 2261/3246* (2013.01); *C08G 2261/414* (2013.01); *H01L 51/0047* (2013.01); *H01L 51/0094* (2013.01); *H01L 51/4253* (2013.01); *Y02E 10/549* (2013.01)

(58) Field of Classification Search
CPC .............. C08G 75/32; C08G 2261/91; H01L 51/0047; Y02E 10/549
USPC .......................... 428/690; 528/377, 378, 380; 252/301.16; 564/426; 549/41, 456, 549/160, 349, 331; 136/263
See application file for complete search history.

(56) References Cited

U.S. PATENT DOCUMENTS

| 2003/0186079 A1* | 10/2003 | Towns et al. .................. 428/690 |
| 2008/0262183 A1 | 10/2008 | Lehmann |
| 2010/0307594 A1 | 12/2010 | Zhu et al. |
| 2011/0284080 A1* | 11/2011 | Gaudiana et al. ............. 136/261 |
| 2012/0018715 A1 | 1/2012 | Moon et al. |
| 2012/0031493 A1 | 2/2012 | Lee et al. |
| 2012/0055536 A1 | 3/2012 | Saito et al. |

FOREIGN PATENT DOCUMENTS

| CN | 101878717 A | 11/2010 |
| CN | 102295752 A | 12/2011 |
| EP | 2110399 A1 | 10/2009 |
| EP | 2264804 A1 | 12/2010 |
| JP | 2009533878 A | 9/2009 |
| JP | 2011099028 A | 5/2011 |
| JP | 2011124551 A | 6/2011 |
| JP | 2011187852 A | 9/2011 |
| KR | 10-2010-0111767 A | 10/2010 |
| KR | 10-2011-0007376 A | 1/2011 |
| KR | 10-1038469 | 6/2011 |
| WO | 2007121252 A2 | 10/2007 |
| WO | 20101135701 A1 | 11/2010 |
| WO | 2011-085004 A2 | 7/2011 |

OTHER PUBLICATIONS

Chang et al. (Journal of Polymer Science Part A: Polymer Chemistry 2012, 50, 271-279).*
Hou et al. (Macromolecules, vol. 42, No. 17, 2009).*
Tang, C.W, "Two-Layer Organic Photovoltaic Cell", Appl. Phys. Lett., 1986, vol. 48, No. 2, pp. 183-185.
Blouin, N. et al., "A Low-Bandgap Poly(2,7-Carbazole) Derivative for Use in High-Performance Solar Cells", Advanced Materials, 2007, vol. 19, No. 17, pp. 2295-2300.
Yu, G. et al., "Polymer Photovoltaic Cells: Enhanced Efficiencies via a Network of Internal Donor-Acceptor Heterojunctions", Science, 1995, vol. 270, pp. 1789-1791.
Journal of Polymer Science, Part A: Polymer Chemistry, vol. 50 (2), p. 271-279.
Journal of Physical Chemistry C, vol. 115 (32), p. 16211-16219.
Journal of Applied Polymer Science, 2011, 123(1), p. 99-107.
Macromolecules, 2012, 45(3), p. 1208-1216.
Chemistry of Materials, 2010, 22(19), p. 5617-5624.
Journal of Physical Chemistry C, 2010, 114(49), p. 21824-21832.
Chemistry of Materials, 2009, 21(19), p. 4669-4675.
Macromolecules, 2010, 43(2), p. 697-708.
Journal of Materials Chemistry, 2011, 21(35), p. 13649-13656.

* cited by examiner

*Primary Examiner* — Shane Fang
(74) *Attorney, Agent, or Firm* — Dentons US LLP

(57) ABSTRACT

A polymer includes a unit of a chemical formula and has a number-average molecular weight of 10,000-1,000,000, and improves the lifespan, efficiency, electrochemical stability and thermal stability of an organic solar cell, and an organic solar cell including a photoactive layer comprising the polymer.

14 Claims, 21 Drawing Sheets

POLYMER AND ORGANIC SOLAR CELL INCLUDING SAME

This application is a National Stage application of International Application No. PCT/KR2013/000919, filed Feb. 5, 2013, and claims priority to and the benefits of Korean Patent Application No. 10-2012-0011980, filed with the Korean Intellectual Property Office on Feb. 6, 2012, Korean Patent Application No. 10-2012-0114808, filed with the Korean Intellectual Property Office on Oct. 16, 2012, and Korean Patent Application No. 10-2013-0012261, filed with the Korean Intellectual Property Office on Feb. 4, 2013, the entire contents of which are incorporated herein by reference.

TECHNICAL FIELD

This application claims priority to and the benefits of Korean Patent Application No. 10-2012-0011980, filed with the Korean Intellectual Property Office on Feb. 6, 2012, Korean Patent Application No. 10-2012-0114808, filed with the Korean Intellectual Property Office on Oct. 16, 2012, and Korean Patent Application No. 10-2013-0012261, filed with the Korean Intellectual Property Office on Feb. 4, 2013, the entire contents of which are incorporated herein by reference.

The present disclosure relates to a polymer and an organic solar cell comprising the same.

BACKGROUND ART

Solar cells are photovoltaic devices that can convert solar energy directly into electrical energy. Solar cells can be divided, according to the type of thin film material thereof, into inorganic solar cells and organic solar cells. A conventional solar cell is made of inorganic crystalline semiconductor material such as silicon (Si), which is doped to form a p-n junction. The electrons and holes created by the absorption of light diffuse to the p-n junction and are accelerated by the electric field to go to electrodes. The power conversion efficiency of this process is defined as the ratio of the electric power provided to the external circuit to the solar power incident on the solar cell. It has reached about 24%, as measured under standard stimulated conditions. However, conventional inorganic solar cells have limitations in terms of economic efficiency and material supply. For this reason, an organic semiconductor solar cell, which is easy to process and inexpensive and has various functions, is receiving attention as a long-term alternative energy source.

In the case of the organic solar cells, various organic semiconductor materials are used in small amounts, and thus material costs can be reduced. In addition, thin films can be formed by a wet process, and thus devices can be easily fabricated.

Meanwhile, it is important to increase the efficiency of solar cells so as to maximize the production of electrical energy from solar energy. In order to increase the efficiency of such solar cells, it is important not only to maximize the production of excitons in a semiconductor, but also to collect the produced charges without loss. One cause of the loss of electric charges is electric charge dissipation caused by the recombination of produced electrons and holes. Various methods for transferring produced electrons or holes to electrodes without loss have been suggested, but require additional processes that can increase the fabrication cost.

Organic solar cells were first introduced in the 1970s, but had no practical use because their efficiency was exceedingly low. However, in 1986, C. W. Tang (Eastman. Kodak) reported a two-layer structure comprising copper phthalocyanine (CuPc) and a perylene tetracarboxylic acid derivative, which could be put to practical use as solar cells, and since then, attention and research on organic solar cells have increased rapidly. In 1995, Yu. et al. introduced the concept of a bulk-heterojunction (BHJ). In addition, fulllerene derivatives having improved solubility, such as PCBM, have been developed for use as n-type semiconductor materials, resulting in a significant improvement in the efficiency of organic solar cells.

DISCLOSURE

Technical Problem

The present disclosure provides a polymer which can show excellent electrical properties thanks to its high hole mobility, and has a stable HOMO energy level, a high open-circuit voltage and excellent photovoltaic conversion efficiency, and an organic solar cell comprising the polymer. The present disclosure also provides an electron donor material which can be produced in large amounts by a simple process.

Technical Solution

One embodiment of the present disclosure provides a polymer comprising a unit of the following chemical formula 1 and having a number-average molecular weight of 10,000-1,000,000:

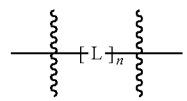

Chemical Formula 1 wherein L comprises structures of the following chemical formulas 2, 3 and 4; and n is an integer ranging from 2 to 100,000,

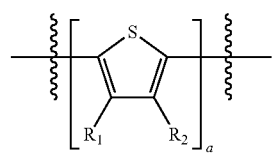

Chemical Formula 2

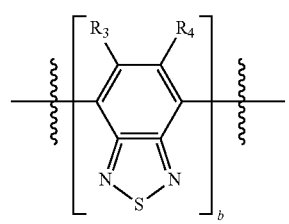

Chemical Formula 3 wherein $R_1$ to $R_4$ are each independently selected from the group consisting of hydrogen; deuterium; a halogen group; a nitro group; a nitrile group; an imide group; an amide group —$CONX_1X_2$, wherein $X_1$ and $X_2$ may be the same or different and are each independently hydrogen, a substituted or unsubstituted $C_{1-25}$ alkyl group or a substituted or unsubstituted $C_{6-25}$ aryl group; a hydroxyl group; an ester group —$COOX_3$, wherein $X_3$ is a substituted or unsubstituted $C_{1-25}$ alkyl group or a substituted or unsubstituted $C_{6-25}$ aryl group; a carbonyl group —$COX_4$, wherein $X_4$ is a substituted or unsubstituted $C_{1-25}$ alkyl group or a substituted or unsubstituted $C_{6-25}$ aryl group; a substituted or unsubstituted $C_{1-25}$ alkyl group; a substituted or unsubstituted $C_{1-25}$ alkoxy group; a substituted or unsubstituted $C_{2-25}$ alkenyl group; a thiophene group unsubstituted or substituted with either a $C_{1-25}$ alkyl group or a $C_{1-25}$ alkoxy group; a selenophene group unsubstituted or substituted with either a $C_{1-25}$ alkyl group or a $C_{1-25}$ alkoxy group; a pyrrole group unsubstituted or substituted with either a $C_{1-25}$ alkyl group or a $C_{1-25}$ alkoxy group; a thiazole group unsubstituted or substituted with either a $C_{1-25}$ alkyl group or a $C_{1-25}$ alkoxy group; an arylamine group unsubstituted or substituted with either a $C_{1-25}$ alkyl group or a $C_{1-25}$ alkoxy group; and an aryl group unsubstituted or substituted with either a $C_{1-25}$ alkyl group or a $C_{1-25}$ alkoxy group;

Chemical Formula 4

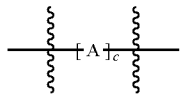

wherein A is one among structures of the following formulas 5 to 13 or a group in which two or more among structures of the following formulas 5 to 13 are bonded to each other, Chemical Formula 5

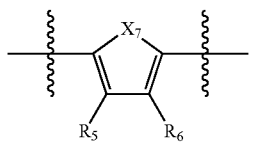

Chemical Formula 6

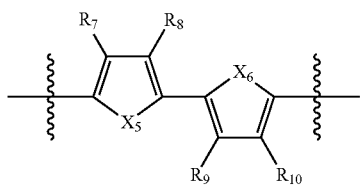

Chemical Formula 7

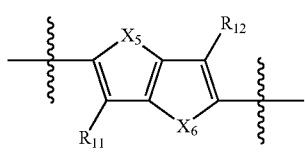

Chemical Formula 8

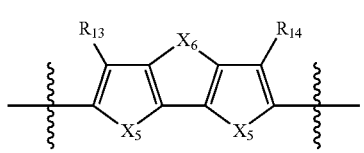

Chemical Formula 9

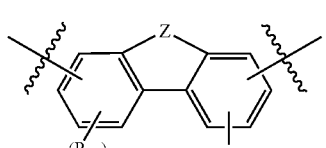

Chemical Formula 10

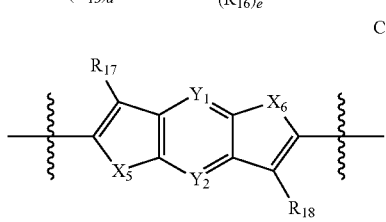

Chemical Formula 11

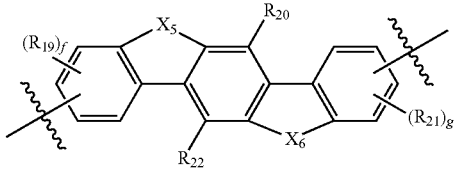

Chemical Formula 12

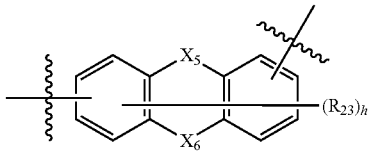

Chemical Formula 13

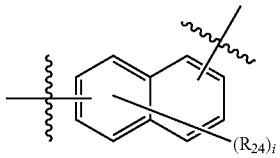

wherein
d, e, f and g are each an integer ranging from 0 to 3,
h and i are each an integer ranging from 0 to 6,
$X_5$ to $X_7$ are each independently selected from the group consisting of CR'R", SiR'R", GeR'R", NR', PR', O, S and Se,
$Y_1$ and $Y_2$ are each independently selected from the group consisting of CR', SiR', GeR', N and P,
Z is selected from the group consisting of SiR'R", GeR'R", NR', PR', O, S and Se,
$R_5$ to $R_{24}$, R', R" and R'" are each independently selected from the group consisting of hydrogen; deuterium; a halogen group; a nitro group; a nitrile group; an imide group; an amide group —$CONX_1X_2$, wherein $X_1$ and $X_2$ may be the same or different and are each independently hydrogen, a substituted or unsubstituted $C_{1-25}$ alkyl group or a substituted or unsubstituted $C_{6-25}$ aryl group; a hydroxyl group; an ester group —$COOX_3$, wherein $X_3$ is a substituted or unsubstituted $C_{1-25}$ alkyl group or a substituted or unsubstituted $C_{6-25}$ aryl group; a carbonyl group —$COX_4$, wherein $X_4$ is a substituted or unsubstituted $C_{1-25}$ alkyl group or a substituted or unsubstituted $C_{6-25}$ aryl group; a substituted or unsubstituted $C_{1-25}$ alkyl group; a substituted or unsubstituted $C_{1-25}$ alkoxy group; a substituted or unsubstituted $C_{2-25}$ alkenyl group; a thiophene group unsubstituted or substituted with either a $C_{1-25}$ alkyl group or a $C_{1-25}$ alkoxy group; a selenophene group unsubstituted or substituted with either a $C_{1-25}$ alkyl group or a $C_{1-25}$ alkoxy group; a pyrrole group unsubstituted or substituted with either a $C_{1-25}$ alkyl group or a $C_{1-25}$ alkoxy group; a thiazole group unsubstituted or substituted with either a $C_{1-25}$ alkyl group or a $C_{1-25}$ alkoxy group; an arylamine group unsubstituted or substituted with either a $C_{1-25}$ alkyl group or a $C_{1-25}$ alkoxy group; and an aryl group unsubstituted or substituted with either a $C_{1-25}$ alkyl group or a $C_{1-25}$ alkoxy group;
a, b and c represent the mole fractions of the structures of formulas 2 to 4, respectively,
a is a real number in the range of $0<a\leq0.45$,
b is a real number in the range of $0<b\leq0.45$,
c is a real number in the range of $0.1\leq c<1$, and
$a+b+c=1$.

Another embodiment of the present disclosure provides an organic solar cell comprising: a first electrode; a second electrode; and one or more photoactive layers, wherein one or more of the photoactive layers comprise the polymer of formula 1.

Still another embodiment of the present disclosure provides a method for fabricating an organic solar cell, the method comprising the steps of: providing a substrate; forming a first electrode on the substrate; forming a photoactive layer comprising the polymer of formula 1 on the first electrode; and forming a second electrode on the photoactive layer.

Advantageous Effects

The polymer represented by formula 1 in the disclosure may be used as a material for an organic layer in organic electronic devices, including organic solar cells. Organic electronic devices such as organic solar cells, which comprise the polymer, exhibit excellent properties, including increased efficiency and stability. In particular, the polymer represented by formula 1 in the present disclosure shows excellent properties, including excellent thermal stability, deep HOMO levels, various bandgaps, various LUMO level states and high electronic stability. The polymer represented by formula 1 in the present disclosure may be used in a pure or impure form in organic electronic devices, including organic solar cells. In addition, it can be applied by a solution coating method, shows improved photovoltaic conversion efficiency, is thermally stable and can improve the life characteristics of the devices.

MODE FOR DISCLOSURE

Figure 1:
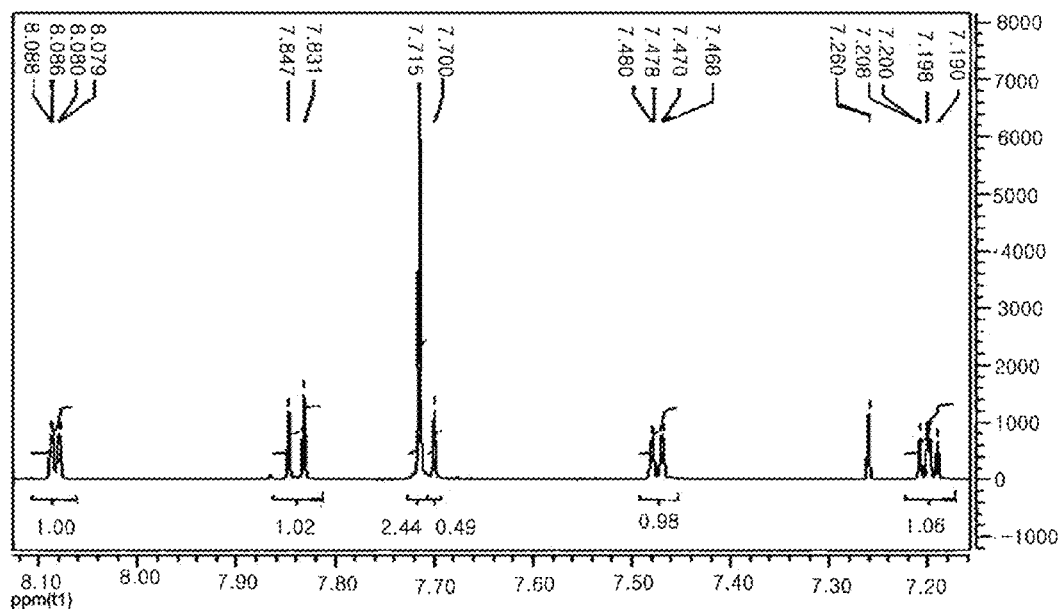
FIG. 1 shows the $^1$H-NMR spectrum of 4-bromo-7-(thiophen-2-yl)-2,1,3-benzothiadiazole prepared in Preparation Example 1-A.

Hereinafter, the present disclosure will be described in detail.

As used herein, the term "electron donor" refers to any ion, atom or molecule that donates an electron to a domain lacking a positive charge or an electron pair. It is also meant to include one that can transfer an excited electron to an electron acceptor having high electronegativity (due to its high ability to receive electrons) when it receives light in the state in which it is mixed with the electron acceptor.

As used herein, the term "electron acceptor" refers to any ion, atom or molecule that receives an electron from an electron donor.

One embodiment of the present disclosure provides a polymer comprising a unit of the following chemical formula 1 and having a number-average molecular weight of 10,000-1,000,000:

Chemical Formula 1

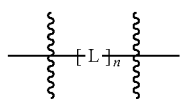

wherein L comprises structures having the following chemical formulas 2, 3 and 4; and n is an integer ranging from 2 to 100,000, Chemical Formula 2

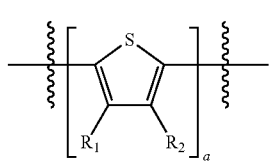

Chemical Formula 3

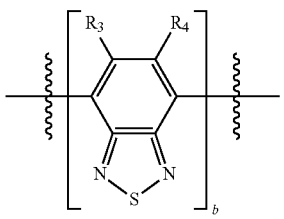

wherein $R_1$ to $R_4$ are each independently selected from the group consisting of hydrogen; deuterium; a halogen group; a nitro group; a nitrile group; an imide group; an amide group —$CONX_1X_2$, wherein $X_1$ and $X_2$ may be the same or different and are each independently hydrogen, a substituted or unsubstituted $C_{1-25}$ alkyl group or a substituted or unsubstituted $C_{6-25}$ aryl group; a hydroxyl group; an ester group —$COOX_3$, wherein $X_3$ is a substituted or unsubstituted $C_{1-25}$ alkyl group or a substituted or unsubstituted $C_{6-25}$ aryl group; a carbonyl group —$COX_4$, wherein $X_4$ is a substituted or unsubstituted $C_{1-25}$ alkyl group or a substituted or unsubstituted $C_{6-25}$ aryl group; a substituted or unsubstituted $C_{1-25}$ alkyl group; a substituted or unsubstituted $C_{1-25}$ alkoxy group; a substituted or unsubstituted $C_{2-25}$ alkenyl group; a thiophene group unsubstituted or substituted with either a $C_{1-25}$ alkyl group or a $C_{1-25}$ alkoxy group; a selenophene group unsubstituted or substituted with either a $C_{1-25}$ alkyl group or a $C_{1-25}$ alkoxy group; a pyrrole group unsubstituted or substituted with either a $C_{1-25}$ alkyl group or a $C_{1-25}$ alkoxy group; a thiazole group unsubstituted or substituted with either a $C_{1-25}$ alkyl group or a $C_{1-25}$ alkoxy group; an arylamine group unsubstituted or substituted with either a $C_{1-25}$ alkyl group or a $C_{1-25}$ alkoxy group; and an aryl group unsubstituted or substituted with either a $C_{1-25}$ alkyl group or a $C_{1-25}$ alkoxy group;

Chemical Formula 4

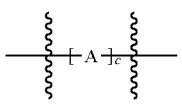

wherein A is one among structures of the following formulas 5 to 13 or a group in which two or more among structures of the following formulas 5 to 13 are bonded to each other, Chemical Formula 5

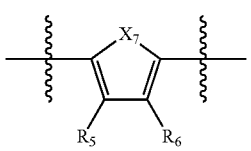

Chemical Formula 6

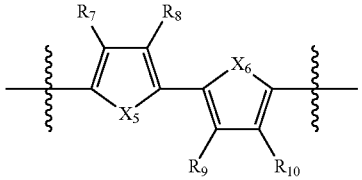

Chemical Formula 7

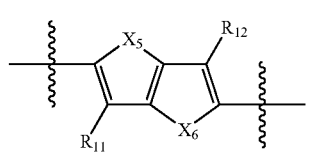

Chemical Formula 8

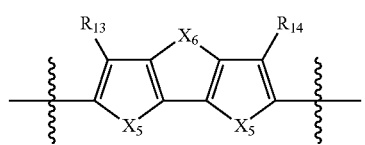

Chemical Formula 9

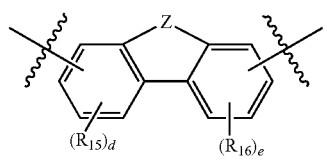

Chemical Formula 10

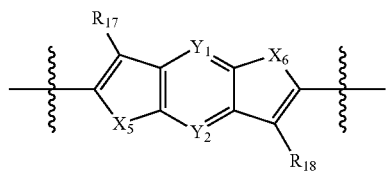

Chemical Formula 11

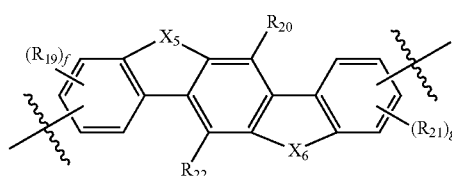

Chemical Formula 12

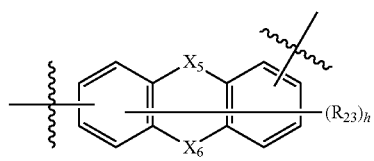

Chemical Formula 13

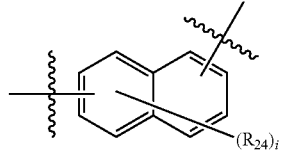

wherein
d, e, f and g are each an integer ranging from 0 to 3,
h and i are each an integer ranging from 0 to 6,
$X_5$ to $X_7$ are each independently selected from the group consisting of CR'R'', SiR'R'', GeR'R'', NR', PR', O, S and Se,
$Y_1$ and $Y_2$ are each independently selected from the group consisting of CR', SiR', GeR', N and P,
Z is selected from the group consisting of SiR'R'', GeR'R'', NR', PR', O, S and Se,
$R_5$ to $R_{24}$, R', R'' and R''' are each independently selected from the group consisting of hydrogen; deuterium; a halogen group; a nitro group; a nitrile group; an imide group; an amide group —$CONX_1X_2$, wherein $X_1$ and $X_2$ may be the same or different and are each independently hydrogen, a substituted or unsubstituted $C_{1-25}$ alkyl group or a substituted or unsubstituted $C_{6-25}$ aryl group; a hydroxyl group; an ester group —$COOX_3$, wherein $X_3$ is a substituted or unsubstituted $C_{1-25}$ alkyl group or a substituted or unsubstituted $C_{6-25}$ aryl group; a carbonyl group —$COX_4$, wherein $X_4$ is a substituted or unsubstituted $C_{1-25}$ alkyl group or a substituted or unsubstituted $C_{6-25}$ aryl group; a substituted or unsubstituted $C_{1-25}$ alkyl group; a substituted or unsubstituted $C_{1-25}$ alkoxy group; a substituted or unsubstituted $C_{2-25}$ alkenyl group; a thiophene group unsubstituted or substituted with either a $C_{1-25}$ alkyl group or a $C_{1-25}$ alkoxy group; a selenophene group unsubstituted or substituted with either a $C_{1-25}$ alkyl group or a $C_{1-25}$ alkoxy group; a pyrrole group unsubstituted or substituted with either a $C_{1-25}$ alkyl group or a $C_{1-25}$ alkoxy group; a thiazole group unsubstituted or substituted with either a $C_{1-25}$ alkyl group or a $C_{1-25}$ alkoxy group; an arylamine group unsubstituted or substituted with either a $C_{1-25}$ alkyl group or a $C_{1-25}$ alkoxy group; and an aryl group unsubstituted or substituted with either a $C_{1-25}$ alkyl group or a $C_{1-25}$ alkoxy group;

a, b and c represent the mole fractions of the structures of formulas 2 to 4, respectively, a is a real number in the range of $0 < a \leq 0.45$, b is a real number in the range of $0 < b \leq 0.45$, c is a real number in the range of $0.1 \leq c < 1$, and $a+b+c=1$.

In the present disclosure, the number-average molecular weight of the polymer is 10,000-1,000,000.

A compound according to one embodiment of the present disclosure is polymeric. A polymeric compound having high number-average molecular weight shows high charge mobility and good film properties compared to an oligomeric compound.

When the number-average molecular weight of the polymer is 10,000 or more, the distance of charge transfer in the molecules will be long, and the frequency of charge hopping between the molecules will be low, so that the charge mobility is prevented from decreasing significantly. Thus, the polymer is suitable for use as an organic layer in an organic solar cell. Also, if the number-average molecular weight of the polymer is 1,000,000 or less, the polymer will have suitable solubility and thus can be applied by a solution process.

Accordingly, a polymer having a number-average molecular weight in the above-described range according to one embodiment of the present disclosure has a charge mobility suitable for a photoactive layer for an organic solar cell and can be applied by a solution process.

In one embodiment of the present disclosure, the polymer having chemical formula 1 comprises the structures of chemical formulas 3 and 2, which are sequentially arranged from left to right in chemical formula 1.

In another embodiment of the present disclosure, the polymer having chemical formula 1 comprises the structures of chemical formulas 2 and 3, which are sequentially arranged from left to right in chemical formula 1.

In one embodiment of the present disclosure, the polymer of chemical formula 1 may be a polymer having the following chemical formula 14 or 15:

Chemical Formula 14

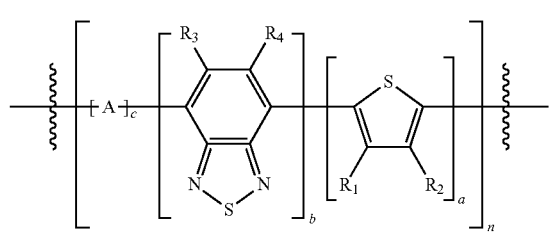

Chemical Formula 15

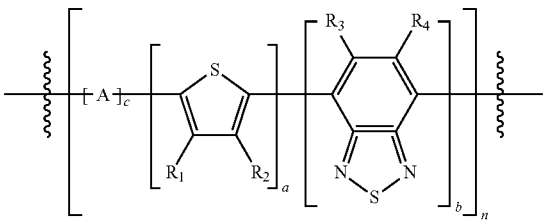

wherein A, $R_1$ to $R_4$, a, b, c and n are as defined in chemical formulas 1 to 4 above.

in the present disclosure indicates a portion that is linked to the main chain, end group or other substituents of the polymer.

In chemical formulas 1 to 15, the halogen group may be fluorine, chlorine, bromine or iodine.

In chemical formulas 1 to 15, the aryl group may be a monocyclic or polycyclic aryl group.

When the aryl group is a monocyclic aryl group, it preferably has 6 to 25 carbon atoms, but is not specifically limited thereto. Specific examples of the monocyclic aryl group include, but are not limited to, phenyl, biphenyl, terphenyl, and stilbenzyl.

When the aryl group is the polycyclic aryl group, it preferably contains 10-24 carbon atoms, but is not specifically limited. Specific examples of the polycyclic aryl group include, but are not limited to, naphthyl, anthryl, phenanthryl, pyrenyl, perylenyl, chrysenyl, and fluorenyl.

In chemical formulas 1 to 15, the amide group preferably has 1 to 25 carbon atoms, but is not specifically limited thereto.

In chemical formulas 1 to 15, the amide group may be mono- or di-substituted with a $C_{1-25}$ straight-chain, branched or cyclic alkyl group or a $C_{6-25}$ aryl group. Specific examples of the amide group include, but are not limited to, compounds having the following structural formulas:

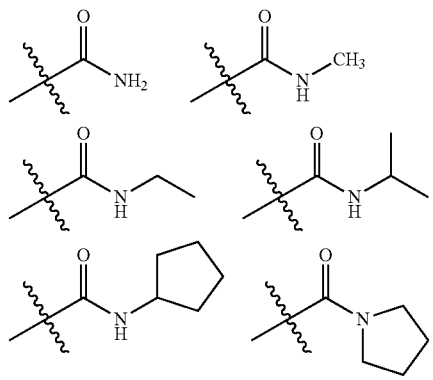

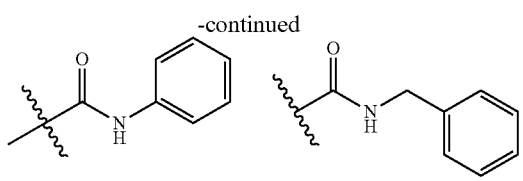

In chemical formulas 1 to 15, the ester group may be substituted with a $C_{1-25}$ straight-chain, branched or cyclic alkyl group or a $C_{6-25}$ aryl group. Specific examples of the ester group include, but are not limited to, compounds having the following structural formulas:

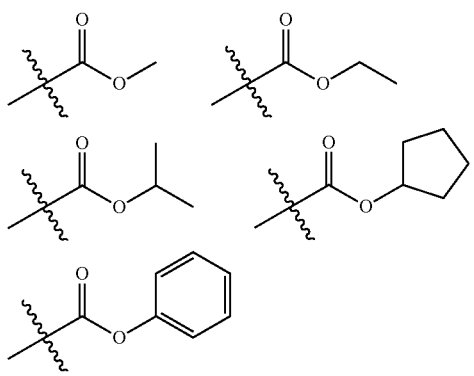

In chemical formulas 1 to 15, the alkyl group may be straight-chain, branched or cyclic. The alkyl group preferably contains 1 to 25 carbon atoms, but is not specifically limited thereto. Specific examples of the alkyl group include, but are not limited to, methyl, ethyl, n-propyl, iso-propyl, n-butyl, sec-butyl, t-butyl, n-pentyl, iso-pentyl, neo-pentyl, n-hexyl, cyclopropyl, cyclobutyl, cyclopentyl, and cyclohexyl.

In chemical formulas 1 to 15, the alkoxy group may be straight-chain, branched or cyclic. The alkoxy group preferably contains 1 to 25 carbon atoms, but is not specifically limited thereto. Specific examples of the alkoxy group include, but are not limited to, methoxy, ethoxy, n-propyloxy, iso-propyloxy, n-butyloxy, and cyclopentyloxy.

In chemical formulas 1 to 15, the alkenyl group may be straight-chain or branched and substituted or unsubstituted, and it may contain 2 to 25 carbon atoms, but is not specifically limited thereto. Specific examples of the alkenyl group include, but are not limited to, ethenyl, propenyl, butenyl, and pentenyl.

In chemical formulas 1 to 15, the term "unsubstituted or substituted" means unsubstituted or substituted with one or more substituents.

In chemical formulas 1 to 15, unless specified otherwise, the substituent may be one or more selected from the group consisting of halogen, nitrile, nitro, hydroxy, alkyl, cycloalkyl, alkenyl, alkoxy, aryloxy, thiol, alkylthio, allylthio, sulfoxy, alkylsulfoxy, arylsulfoxy, silyl, boron, arylamine, aralkylamine, alkylamine, aryl, fluorenyl, carbazole, arylalkyl, arylalkenyl, heterocyclic and acetylene groups.

In chemical formulas 2 to 4 according to one embodiment of the present disclosure, a, b and c may represent the mole fractions of the compounds of formulas 2 to 4, respectively. As used herein, the term "mole fraction" refers to the ratio of the moles of any compound to the total moles of all compounds present.

In one embodiment of the present disclosure, a in chemical formula 1, 14 or 15 is the ratio of the moles of the compound of chemical formula 2 to the total moles of all the compounds, and may be $0<a\leq 0.45$.

In one embodiment of the present disclosure, b in chemical formula 1, 14 or 15 is the ratio of the moles of the compound of chemical formula 3 to the total moles of all the compounds, and may be $0<b\leq 0.45$.

In one embodiment of the present disclosure, c in chemical formula 1, 14 or 15 is the ratio of the moles of the compound of chemical formula 4 to the total moles of all the compounds, and may be $0.1\leq c<1$.

In one embodiment of the present disclosure, a+b+c may be 1.

In one embodiment of the present disclosure, a may be ⅓, b may be ⅓, and c may be ⅓.

In chemical formula 1, 14 or 15 according to one embodiment of the present disclosure, n may be an integer ranging from 2 to 100,000, preferably from 30 to 100. When n is 100,000 or less, the polymer can be easily applied by a solution coating method. When n ranges from 2 to 100,000, the mechanical and electrical properties of the polymer can be improved by increasing the value of n. Specifically, when n is an integer ranging from 30 to 100, the polymer will have good solubility, and thus will be easily applied by a solution coating method.

In chemical formula 1, 14 or 15 according to one embodiment of the present disclosure, the polymer may have a number-average molecular weight of 10,000-1,000,000 and a molecular weight distribution of 1-100. Preferably, the polymer has a number-average molecular weight of 10,000-100,000 and a molecular weight distribution of 1-3.

When the number-average molecular weight is 1,000,000 or less, the polymer will have good solubility, and thus can be easily applied by a solution coating process. When the number-average molecular weight ranges from 10,000 to 1,000,000, the electrical and mechanical properties of the polymer improve with increases in the number-average molecular weight. Specifically, when the number-average molecular weight ranges from 10,000 to 100,000, the polymer will have increased solubility and improved electrical and mechanical properties.

As used herein, the term "number-average molecular weight" refers to a value obtained by dividing the mass by the total number of polymer chains in the polymer.

The molecular weight distribution of the polymer is preferably in the range from 1 to 100. When the molecular weight distribution is 100 or less, the effect of the polymer becomes better with a decrease in the molecular weight distribution. Specifically, when the molecular weight distribution is 1-3, the polymer will have good solubility, so that it is easily applied by a solution coating method and has improved electrical and mechanical properties.

As used herein, the term "molecular weight distribution" refers to the value obtained by dividing the weight-average molecular weight (Mw) by the number-average molecular weight (Mn).

In chemical formula 1, 14 or 15 according to one embodiment of the present disclosure, end groups are not specifically limited, and examples thereof include heteroaromatic groups, aromatic groups, halogen-substituted alkyl groups and the like. The heteroaromatic groups include thiophene, furan and the like. The aromatic groups include benzene, naphthalene, anthracene and the like. However, the scope of the end group is not limited to this embodiment.

In one embodiment of the present disclosure, A is the compound of chemical formula 9.

In one embodiment of the present disclosure, A is the compound of chemical formula 9 while Z is NR'.

In one embodiment of the present disclosure, A is the compound of chemical formula 9 while Z is NR', wherein R' is a substituted or unsubstituted $C_{2-25}$ alkyl group.

In one embodiment of the present disclosure, A is the compound of chemical formula 9 while Z is NR', wherein R' is a branched chain alkyl group.

In one embodiment of the present disclosure, A is the compound of chemical formula 8.

In one embodiment of the present disclosure, A is the compound of chemical formula 8 while $X_1$ is S.

In one embodiment of the present disclosure, A is the compound of chemical formula 8 while $X_2$ is SiR'R".

In one embodiment of the present disclosure, A is the compound of chemical formula 8 while $X_2$ is SiR'R", wherein R' is a substituted or unsubstituted $C_{1-25}$ alkyl group.

In one embodiment of the present disclosure, A is the compound of chemical formula 8 while $X_2$ is SiR'R", wherein R' is a branched-chain alkyl group.

In one embodiment of the present disclosure, A is the compound of chemical formula 8 while $X_2$ is SiR'R", wherein R" is a substituted or unsubstituted $C_{1-25}$ alkyl group.

In one embodiment of the present disclosure, A is the compound of chemical formula 8 while $X_2$ is SiR'R", wherein R" is a branched-chain alkyl group.

In one embodiment of the present disclosure, A is the compound of chemical formula 8 while $X_2$ is CR'R".

In one embodiment of the present disclosure, A is the compound of chemical formula 8 while $X_2$ is CR'R", wherein R' is a substituted or unsubstituted $C_{1-25}$ alkyl group.

In one embodiment of the present disclosure, A is the compound of chemical formula 8 while $X_2$ is CR'R", wherein R' is a branched-chain alkyl group.

In one embodiment of the present disclosure, A is the compound of chemical formula 8 while $X_2$ is CR'R", wherein R" is a substituted or unsubstituted $C_{1-25}$ alkyl group.

In one embodiment of the present disclosure, A is the compound of chemical formula 8 while $X_2$ is CR'R", wherein R" is a branched-chain alkyl group.

In one embodiment of the present disclosure, A is the compound of chemical formula 10.

In one embodiment of the present disclosure, A is the compound of chemical formula 10 while $X_1$ is S.

In one embodiment of the present disclosure, A is the compound of chemical formula 10 while $X_2$ is S.

In one embodiment of the present disclosure, A is the compound of chemical formula 10 while $Y_1$ is CR'.

In one embodiment of the present disclosure, A is the compound of chemical formula 10 while $Y_1$ is CR', wherein R' is a substituted or unsubstituted $C_{1-25}$ alkoxy group.

In one embodiment of the present disclosure, A is the compound of chemical formula 10 while $Y_1$ is CR', wherein R' is a branched-chain alkoxy group.

In one embodiment of the present disclosure, A is the compound of chemical formula 10 while $Y_2$ is CR'.

In one embodiment of the present disclosure, A is the compound of chemical formula 10 while $Y_2$ is CR', wherein R' is a substituted or unsubstituted $C_{1-25}$ alkoxy group.

In one embodiment of the present disclosure, A is the compound of chemical formula 10 while $Y_2$ is CR', wherein R' is a branched-chain alkoxy group.

In one embodiment of the present disclosure, $R_1$ is hydrogen.

In one embodiment of the present disclosure, $R_2$ is hydrogen.

In one embodiment of the present disclosure, $R_1$ is a substituted or unsubstituted $C_{1-25}$ alkoxy group.

In one embodiment of the present disclosure, $R_2$ is a substituted or unsubstituted $C_{1-25}$ alkoxy group.

In one embodiment of the present disclosure, A is the compound of chemical formula 5.

In one embodiment of the present disclosure, A is the compound of chemical formula 5 while $X_7$ is S.

In one embodiment of the present disclosure, $R_5$ is hydrogen.

In one embodiment of the present disclosure, $R_6$ is hydrogen.

In one embodiment of the present disclosure, $R_3$ and $R_4$ are the same or different and each independently hydrogen or a substituted or unsubstituted $C_{1-25}$ alkoxy group. When $R_3$ or $R_4$ is an alkoxy group, the solubility of the polymer can increase.

In one embodiment of the present disclosure, $R_1$ is hydrogen.

In one embodiment of the present disclosure, $R_2$ is hydrogen.

The polymer of chemical formula 1 according to one embodiment of the present disclosure may be one represented by any one of the following structural formulas 1 to 14, but is not limited thereto:

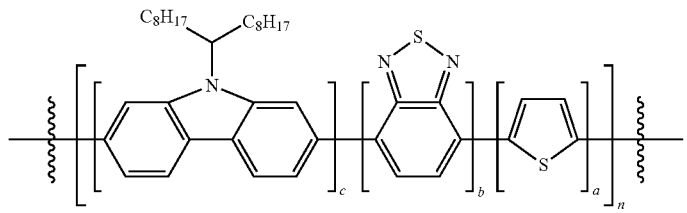

Structural Formula 1

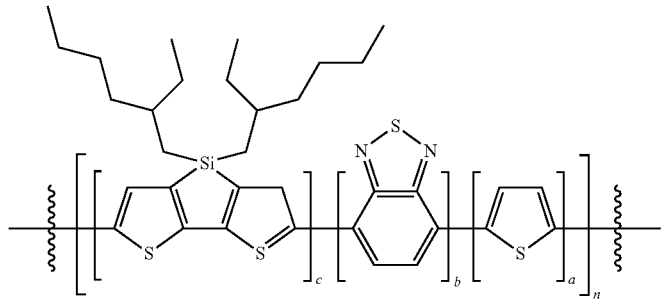

Structural Formula 2

-continued
Structural Formula 3
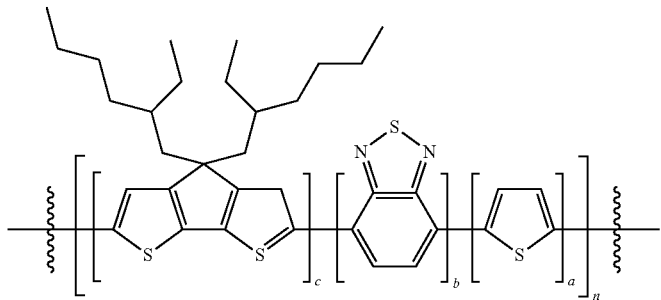
Structural Formula 4
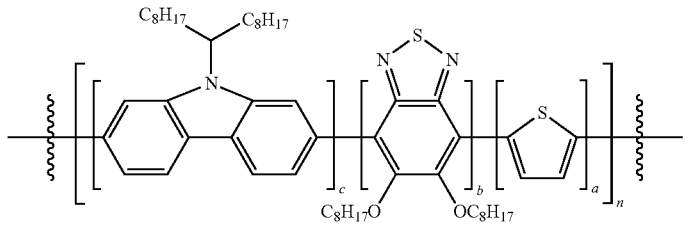
Structural Formula 5
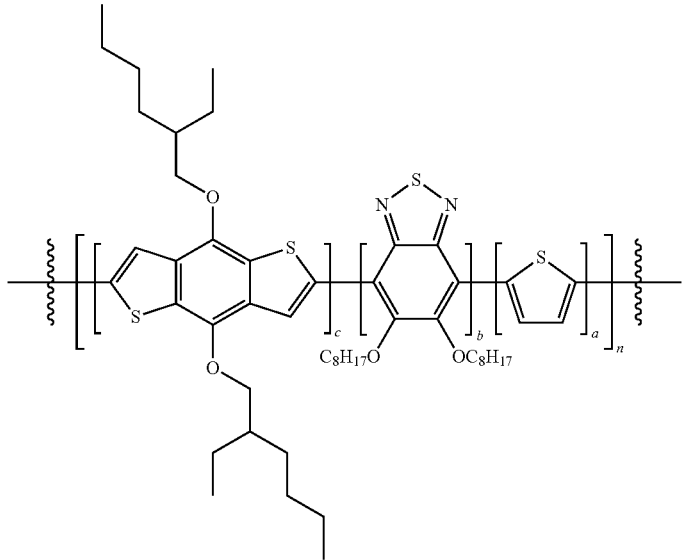
Structural Formula 6
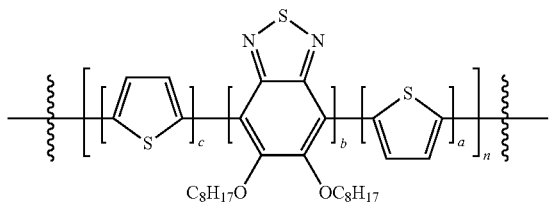
Structural Formula 7
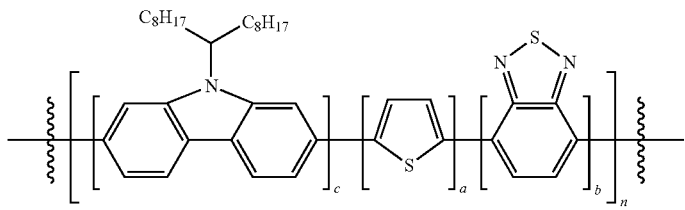

-continued
Structural Formula 8
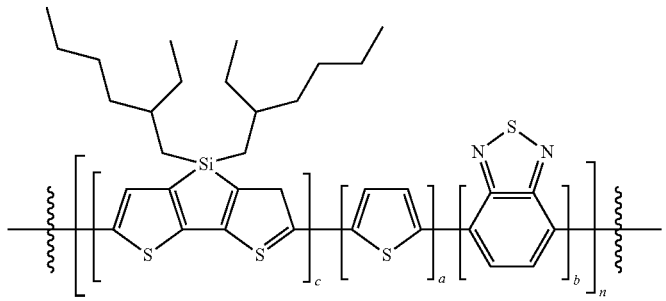
Structural Formula 9
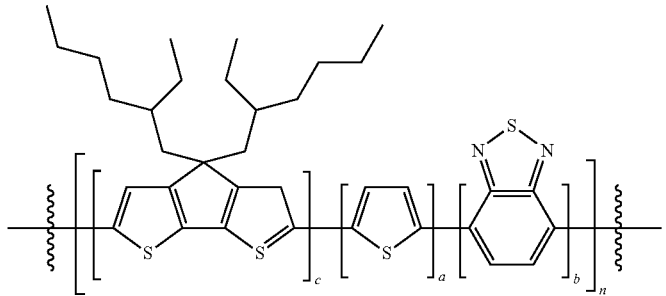
Structural Formula 10
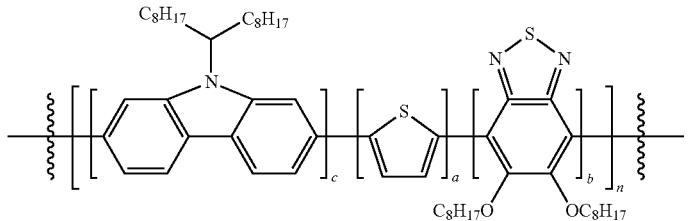
Structural Formula 11
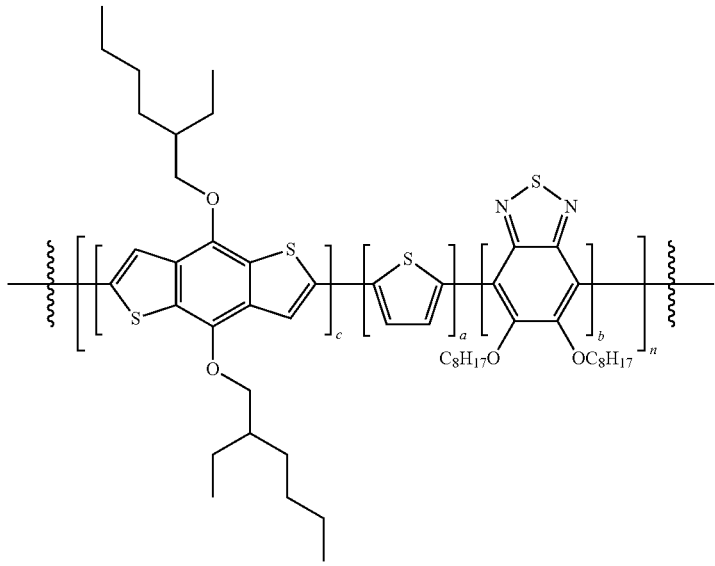
Structural Formula 12
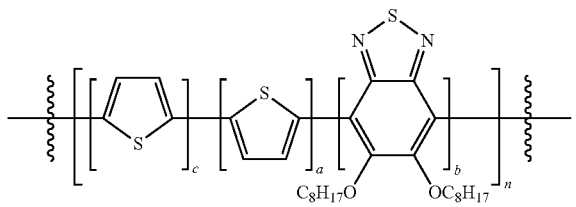

Structural Formula 13

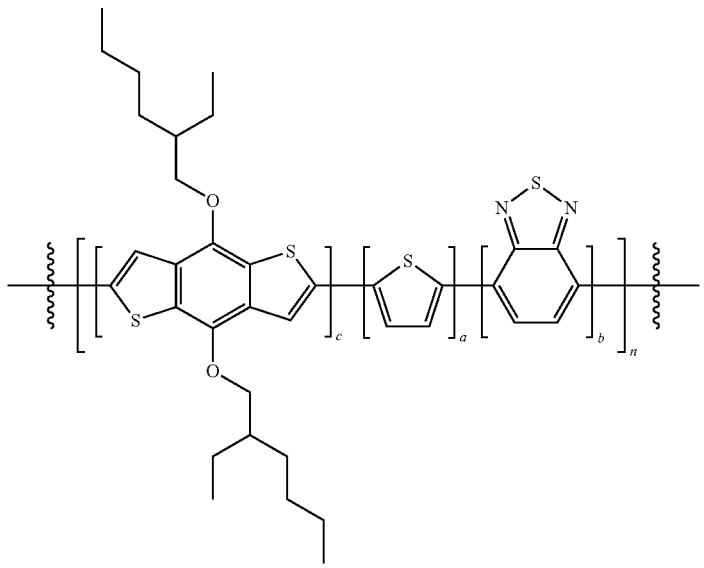

Structural Formula 14

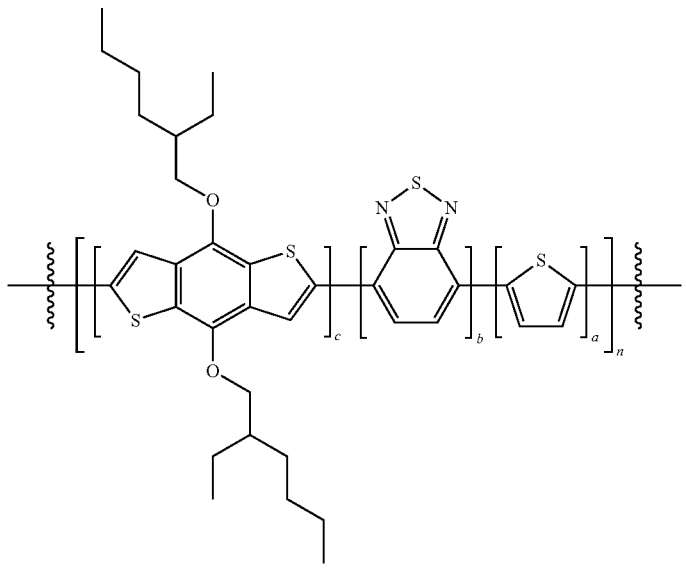

wherein a, b, c and n are as defined in chemical formulas 1 to 4 above.

The compound of chemical formula 1 according to one embodiment of the present disclosure can be prepared through a multi-step chemical reaction. Specifically, monomers can be prepared by an alkylation reaction, the Grignard reaction, the Suzuki coupling reaction or the Stille coupling reaction, after which final polymers can be prepared from the monomers by a carbon-carbon coupling reaction such as the Stille coupling reaction. When the substituent to be introduced is a boronic acid or boronic ester compound, the polymer can be prepared by the Suzuki coupling reaction, and when the substituent to be introduced is a tributyltin compound, the polymer can be prepared by the Stille coupling reaction, but is not limited thereto.

One embodiment of the present disclosure provides an organic solar cell comprising a photoactive layer which comprises a polymer comprising the unit of chemical formula 1.

An organic solar cell according to one embodiment of the present disclosure comprises a first electrode, a second electrode, and a photoactive layer. The organic solar cell may further comprise a substrate, a hole transport layer and/or an electrode transport layer.

The organic solar cell according to the embodiment of the present disclosure further comprises one or more of an electrode transport layer and a hole transport layer.

In another embodiment, one or more of the electron transport layer and the hole transport layer comprise the polymer of chemical formula 1.

The substrate may be a glass substrate or a transparent plastic substrate, which have excellent transparency, surface smoothness, ease of handling and water resistance properties, but is not limited thereto. Any substrate may be used without limitation in the present disclosure, as long as it is commonly used in organic solar cells. Specific examples of the substrate include, but are not limited to, PET (polyethylene terephthalate), PEN (polyethylene naphthalate), PP (polypropylene), PI (polyimide) and TAC (triacetyl cellulose) substrates.

The first electrode may be an anode or a cathode, and the second electrode may be an anode or a cathode.

The anode is preferably made of a material having a high work function such that holes are easily injected into the organic layer. In addition, the anode may be made of a transparent, highly conductive material, but is not limited thereto. Specific examples of the anode material that may be used in the present disclosure include, but are not limited to, metals or alloys thereof, such as vanadium, chromium, copper, zinc or gold; metal oxides such as zinc oxide, indium oxide, indium tin oxide (ITO), tin oxide ($SnO_2$), zinc oxide (ZnO), or indium zinc oxide (IZO); metal/oxide combinations such as ZnO:Al or $SnO_2$:Sb; and conductive polymers such as poly(3-methylthiophene), poly[3,4-(ethylene-1,2-dioxy)thiophene] (PEDOT), polypyrrole or polyaniline.

The cathode is preferably made of a material having a low work function such that electrons are easily injected into the organic layer. Specific examples of the cathode material include, but are not limited to, metals or alloys thereof, such as magnesium, calcium, sodium, potassium, titanium, indium, yttrium, lithium, gadolinium, aluminum, silver, tin or lead; and multilayer materials, such as Al/Li, $Al/BaF_2$, $Al/BaF_2$/Ba, LiF/Al or $LiO_2$/Al.

The hole transport layer and/or the electron transport layer may be made of a material which efficiently transfers electrons and holes to the photoactive layer to increase the mobility of produced charges to the electrodes, but is not limited thereto. Specific examples of materials for forming the hole transport layer and/or the electron transport layer include, but are not limited to, arylamine-based organic materials, conductive polymers, and block polymers comprising a conjugated moiety and a non-conjugated moiety. Examples of the material for the hole transport layer include PEDOT:PSS (poly(3,4-ethylenediocythiophene) doped with poly(styrenesulfonic acid)), and N,N'-bis(3-methylphenyl)-N,N'-diphenyl-[1,1'-biphenyl]-4,4'-diamine (TPD).

Examples of the material for the electron transport layer include an Al complex of 8-hydroxyquinoline; a complex containing $Alq_3$; organic radical compounds; a hydroxyflavone-metal complex; aluminum trihydroxyquinoline ($Alq_3$); the 1,3,4-oxadiazole derivative PBD (2-(4-biphenyl)-5-phenyl-1,3,4-oxadiazole); the quinoxaline derivative TPQ (1,3,4-tris[(3-phenyl-6-trifluoromethyl)qunoxaline-2-yl]benzene; and triazole derivatives.

The photoactive layer may comprise an electrode donor material and an electrode acceptor material. The electron donor material may be the polymer of chemical formula 1 according to one embodiment of the present disclosure. The electron acceptor material may be selected from the group consisting of fullerene, fullerene derivatives, vasocuproin, semiconductor elements, semiconductor compounds, or combinations thereof. Specifically, the electron acceptor material may be phenyl $C_{61}$-butyric acid methyl ester ($PC_{61}BM$) or phenyl $C_{71}$-butyric acid methyl ester ($PC_{71}BM$).

The electron donor material and the electron acceptor material in the photoactive layer can form a bulk heterojunction (BHJ). The electron donor material and the electron acceptor material may be mixed with each other at a ratio of 1:10-10:1 (w/w). After the electron donor material and the electron acceptor material have been mixed, they may be annealed at a temperature of 30 to 300° C. for 1 second to 24 hours in order to maximize the characteristics thereof.

The organic solar cell may comprise the anode, the hole transport layer, the photoactive layer, the electron transport layer and the cathode, which are sequentially arranged from bottom to top. Alternatively, the organic solar cell may also comprise the cathode, the electron transport layer, the photoactive layer, the hole transport layer and the anode, which are sequentially arranged from bottom to top. However, the scope of the present disclosure is not limited to this arrangement.

In the organic solar cell, an exciton consisting of a pair of an electron and a hole is formed in the p-type semiconductor by light excitation and is separated into an electron and a hole at the p-n junction. The separated electron and hole move to the n-type semiconductor thin film and the p-type semiconductor thin film, respectively, and are collected in the first and second electrode, respectively, so that they can be used as electrical energy.

Organic solar cells are divided, according to the structure of a photoactive layer, into a bi-layer p-n junction organic solar cell and a BHJ (bulk heterojunction) organic solar cell. The bi-layer p-n junction organic solar cell comprises a two-layer photoactive layer consisting of a p-type semiconductor thin film and an n-type semiconductor thin film. The BHJ (bulk heterojunction) organic solar cell comprises a photoactive layer consisting of a blend of an n-type semiconductor and a p-type semiconductor.

The efficiency of polymer solar cells has been significantly improved through new device configurations and changes in process conditions. Thus, there have been studies on the development of new electron donor materials having a low bandgap and new electron acceptor materials having high charge mobility as substitutes for conventional materials.

Electron donor materials have been studied with a focus on p-type conductive polymer, but do not absorb a significant portion of the solar light spectrum due to their high bandgap. In addition, these materials have poor solubility, which limits the use of a solution coating process, a spin coating process, a roll-to-roll process or an inkjet printing process. Meanwhile, BHJ devices comprising electron acceptor materials such as fullerene derivatives have an efficiency of up to 8%, and thus the development of novel photoactive materials having improved electronic properties for commercialization has been required.

However, an organic solar cell according to one embodiment of the present disclosure shows excellent properties in terms of efficiency and stability. The polymer of chemical formula 1 according to the present disclosure shows excellent properties, including excellent thermal stability, deep HOMO levels, various bandgap, various LUMO level states and high electronic stability. The polymer of chemical formula 1 according to the present disclosure has excellent solubility, and can thereby be applied to organic electronic devices, including organic solar cells, using a solution coating process. In addition, it shows improved photovoltaic conversion efficiency, is thermally stable, and can increase the lifespan of the devices.

The organic solar cell according to the present disclosure can be fabricated using the materials and methods known in the art, except that the photoactive layer comprises the compound of the present disclosure, that is, the heteroaromatic polymer compound represented by chemical formula 1.

In accordance with one embodiment of the present disclosure, there is provided a method for fabricating an organic solar cell, the method comprising the steps of: providing a substrate; forming a first electrode on the substrate; forming a photoactive layer comprising the polymer of chemical formula 1 on the first electrode; and forming a second electrode on the photoactive layer.

The method for fabricating the organic solar cell according to one embodiment of the present disclosure further comprises, after the step of forming the first electrode, but before the step of forming the photoactive layer, a step of forming a hole transport layer on the first electrode.

A method for fabricating an organic solar cell according to another embodiment of the present disclosure comprises the steps of: providing a substrate; forming an anode on the substrate; forming a photoactive layer on the anode; and forming a cathode on the photoactive layer.

A method for fabricating an organic solar cell according to still another embodiment of the present disclosure comprises the steps of: providing a substrate; forming a cathode on a substrate; forming a photoactive layer on the cathode; and forming an anode on the photoactive layer.

The organic solar cell of the present disclosure can be fabricated, for example, by sequentially depositing the anode, the photoactive layer and the cathode on the substrate. Herein, the deposition can be performed using wet coating methods, including gravure printing, offset printing, screen printing, inkjet printing, spin coating, and spray coating, but is not limited thereto.

Hereinafter, a method for preparing the heteroaromatic polymer compound of chemical formula 1, and a method for fabricating an organic solar cell using the polymer compound will be described in detail with reference to preparation examples, examples, comparative examples and test examples. It is to be understood, however, that these preparation examples, examples, comparative examples and test examples are for illustrative purposes only and are not intended to limit the scope of the present disclosure.

Preparation Example 1-A

Preparation of monomer
(4-bromo-7-(thiophen-2-yl)2,1,3-benzothiadiazole)

Preparation Example 1-A

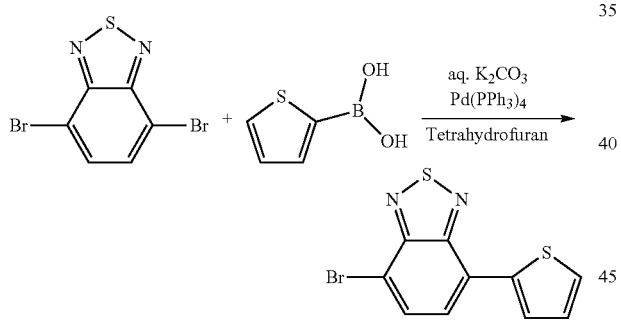

In this Example, 4,7-dibromo-2,1,3-benzothiadiazole was prepared with reference to the literature (X. Li, W, Zeng, Y, Zhang, Q. Hou, W. Yang and Y. Cao, Eur. Polymer. U., 2005, 41, 2923-2933).

4,7-Dibromo-2,1,3-benzothiadiazole (1 g, 3.40 mmol), 2-thiopheneboronic acid (0.435 g, 3.40 mmol), 2M $K_2CO_3$ aqueous solution and (tetrakis(triphenylphosphine)palladium(0) (372 mg, 0.340 mmol) were added to and dissolved in 20 ml of tetrahydrofuran (THF) and stirred under reflux. After 24 hours, the mixture was cooled to room temperature, and THF was removed in a vacuum. The residue was extracted with chloroform, washed with water and dried using $MgSO_4$. The solution was filtered through silica gel to remove the catalyst, followed by the removal of the chloroform. The residue was recrystallized from methanol and dichloromethane to afford 0.6 g of a yellow solid.

Yield: 59%.

$^1$H-NMR (500 MHz, $CDCl_3$): d (ppm) 8.08 (d, J=3.0 Hz, 1H), 7.84 (d, J=8.0 Hz, 1H), 7.71 (d, J=7.5 Hz, 1H), 7.47 (d, J=4.0 Hz, 8H), 7.20 (t, J=9.0 Hz, 1H).

MS: [M+H]$^+$=297.

FIG. 1 shows the $^1$H-NMR spectrum of (4-bromo-7-(thiophen-2-yl)-2,1,3-benzothiadiazole) synthesized in Preparation Example 1-A.

Preparation Example 1-B

Preparation of monomer (4-bromo-7-(5-bromothiophen-2-yl-2,1,3-benzothiadiazole)

Preparation Example 1-B

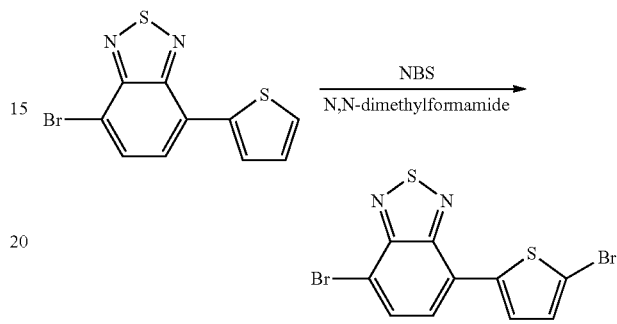

4-Bromo-7-(thiophen-2-yl)-2,1,3-benzothiadiazole (0.7 g, 2.36 mmol) was added to and dissolved in 25 ml of dimethylformamide (DMF), and N-bromosuccinimide (1.26 g, 7.07 mmol) was added thereto, followed by stirring for 12 hours. Water was added to the reaction solution, and the precipitated was filtered. The solution was washed with acetone, after which the solvent was removed.

Yield: 72%.

$^1$H-NMR (500 MHz, $CDCl_3$): d (ppm) 7.84 (s, 1H), 7.78 (s, 1H), 7.63 (s, 1H), 7.15 (s, 1H).

MS: [M+H]$^+$=376.

Figure 2:
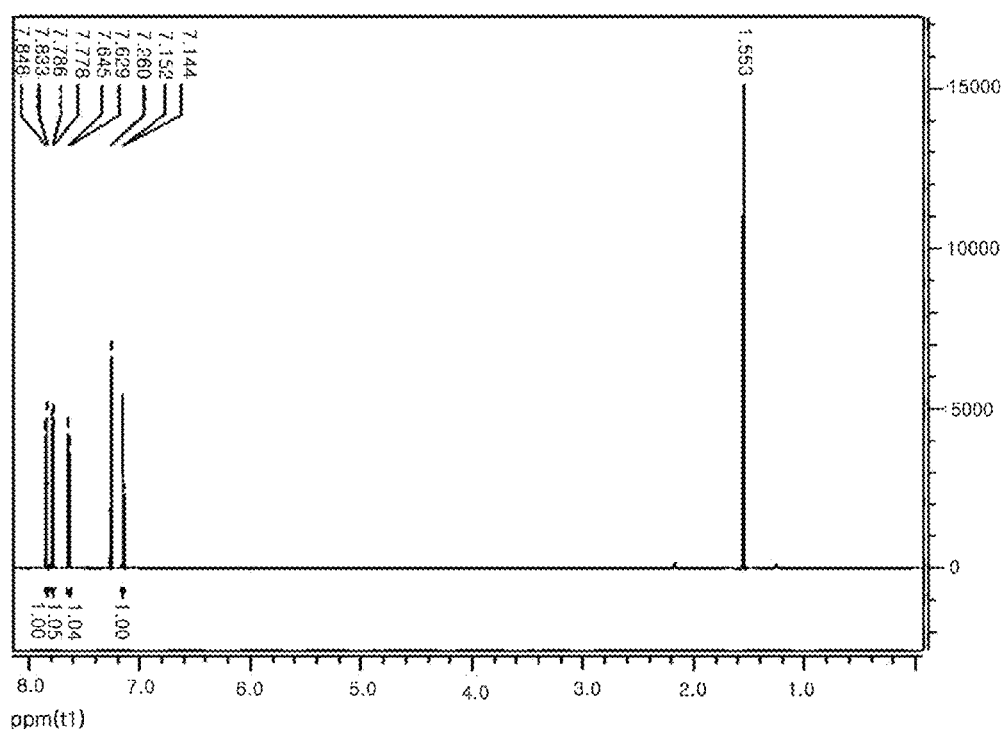
FIG. 2 shows the $^1$H-NMR spectrum of 4-bromo-7-(5-bromothiophen-2-yl)-2,1,3-benzothiadiazole prepared in Preparation Example 1-B.

FIG. 2 shows the $^1$H-NMR spectrum of 4-bromo-7-(5-bromothiophen-2-yl)-2,1,3-benzothiadiazole prepared in Preparation Example 1-B.

Figure 3:
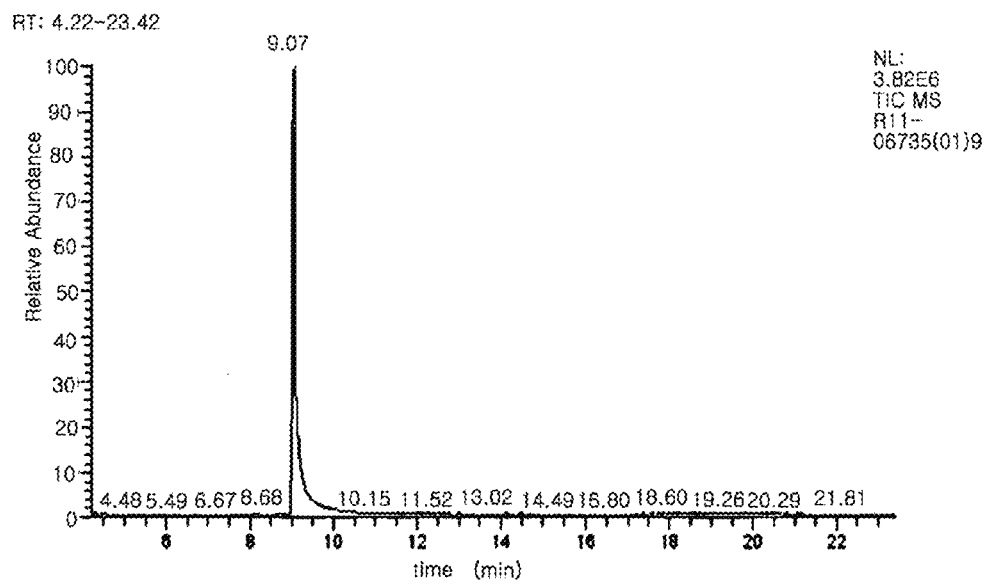
FIG. 3 shows the HPLC-MS spectrum of 4-bromo-7-(5-bromothiophen-2-yl)-2,1,3-benzothiadiazole prepared in Preparation Example 1-B.
Figure 3:
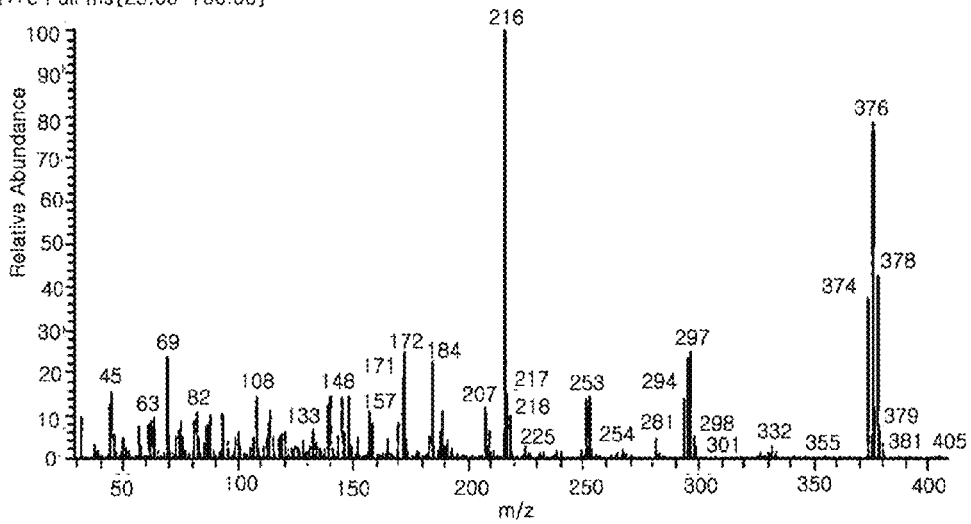

FIG. 3 shows the HPLC-MS spectrum of 4-bromo-7-(5-bromothiophen-2-yl)-2,1,3-benzothiadiazole prepared in Preparation Example 1-B.

Preparation Example 1-C

Preparation of monomer
(2,5-bis(trimethylstannyl)thiophene)

Preparation Example 1-C

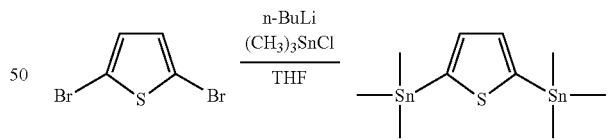

2,5-dibromothiophene (9.68 g, 40.0 mmol) was dissolved in 200 ml of tetrahydrofuran (THF) and cooled to −78° C. 1.6M n-butyllithium in hexane (55 ml, 88 mmol) was added slowly to the solution at that temperature and stirred for 1 hour. Then, 1M trimethyltinchloride in THF (100 ml, 100 mmol) was added thereto at one time, and the mixture was warmed to room temperature and stirred for 12 hours. The solution was poured onto ice, extracted three times with diethyl ether, washed three times with water, and dried with $MgSO_4$ (magnesium sulfate). The solvent was removed under reduced pressure, and the residue was recrystallized from methanol to afford a white solid.

Yield: 73.1%.

Figure 10:
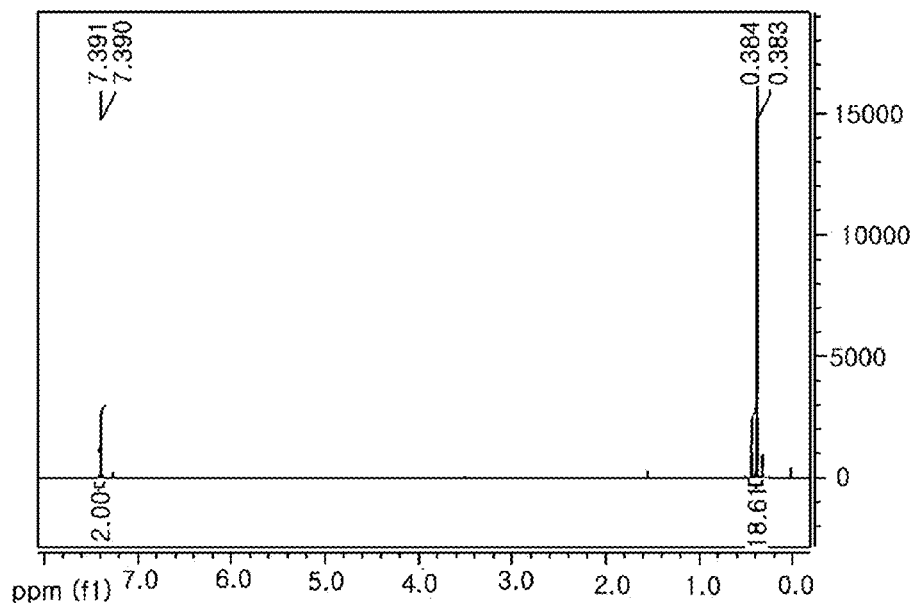
FIG. 10 shows the $^1$H-NMR spectrum of 2,5-bis(trimethylstannyl)thiophene prepared in Preparation Example 1-C.

FIG. 10 shows the NMR spectrum of 2,5-bis(trimethylstannyl)thiophene prepared in Preparation Example 1-C.

Preparation Example 1-D

Preparation of monomer (4-bromo-7-(thiophen-2-yl)-5,6-bis(octyloxy)benzo[c]-1,2,5-thiadiazole)

Preparation Example 1-D

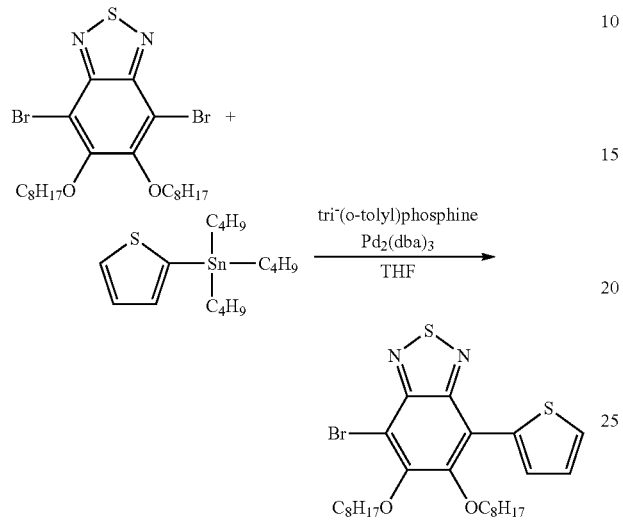

In this Example, 4,7-dibromo-5,6-bis(octyloxy)benzo[c]-1,2,5-thiadiazole was prepared with reference to the literature (Wonho Lee, Hyosung Choi, Sungu Hwang, Jin Young Kim and Han Young Woo, Chem. Eur. J. 18, 2012, 2551-2558).

2-(tributylstannyl)thiophene (3.39 g, 9.08 mmol), 4,7-dibromo-5,6-bis(octyloxy)benzo[c]-1,2,5-thiadiazole (0.500 g, 9.08 mmol), tri-(o-tolyl)phosphine (331 mg) and Pd$_2$(dba)$_3$ (tris(dibenzylideneacetone)dipalladium(0) (249 mg) were added to and dissolved in 10 ml of tetrahydrofuran (THF) and stirred under reflux. After 24 hours, the mixture was cooled to room temperature, and THF was removed in a vacuum. The residue was extracted with dichloromethane, washed with water, and then dried using MgSO$_4$. The resulting material was purified by column chromatography to afford a yellow solid.

Yield: 49%.

Figure 11:
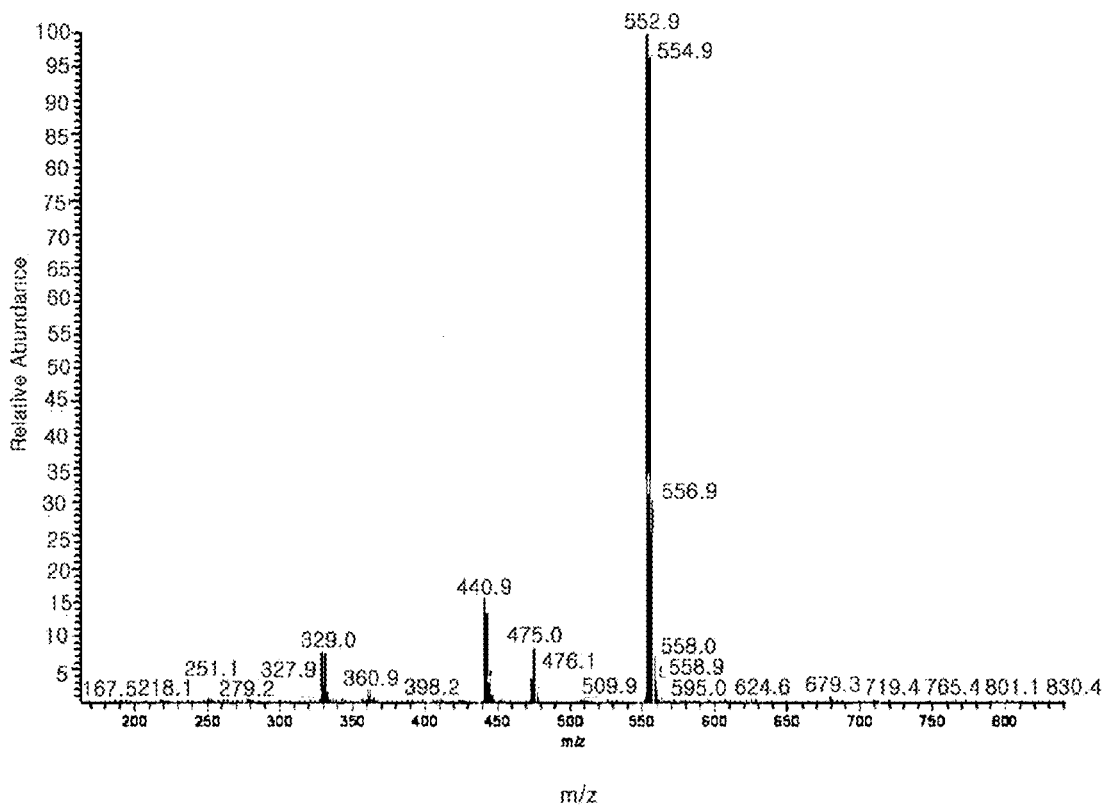
FIG. 11 shows the MS spectrum of 4-bromo-7-(thiophen-2-yl)-5,6-bis(octyloxy)benzo[c]-1,2,5-thiadiazole prepared in Preparation Example 1-D.

FIG. 11 shows the MS spectrum of 4-bromo-7-(thiophen-2-yl)-5,6-bis(octyloxy)benzo[c]-1,2,5-thiadiazole prepared in Preparation Example 1-D.

Preparation Example 1-E

Preparation of monomer (4-bromo-7-(5-bromothiophen-2-yl)-5,6-bis(octyloxy)benzo[c]-1,2,5-thiadiazole)

Preparation Example 1-E

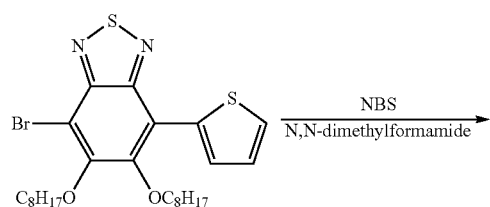

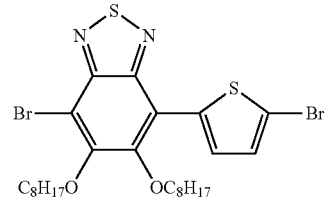

4-bromo-7-(thiophen-2-yl)-5,6-bis(octyloxy)benzo[c]-1,2,5-thiadiazole (1.22 g, 2.19 mmol) was added to and dissolved in 30 ml of dimethylformamide (DMF), and N-bromosuccinimide (0.429 g, 2.41 mmol) was added thereto, followed by stirring for 12 hours. The mixture was extracted with dichloromethane, washed with water, and then dried using MgSO$_4$. The resulting material was purified by column chromatography to afford a yellow solid.

Yield: 67%.

Figure 12:
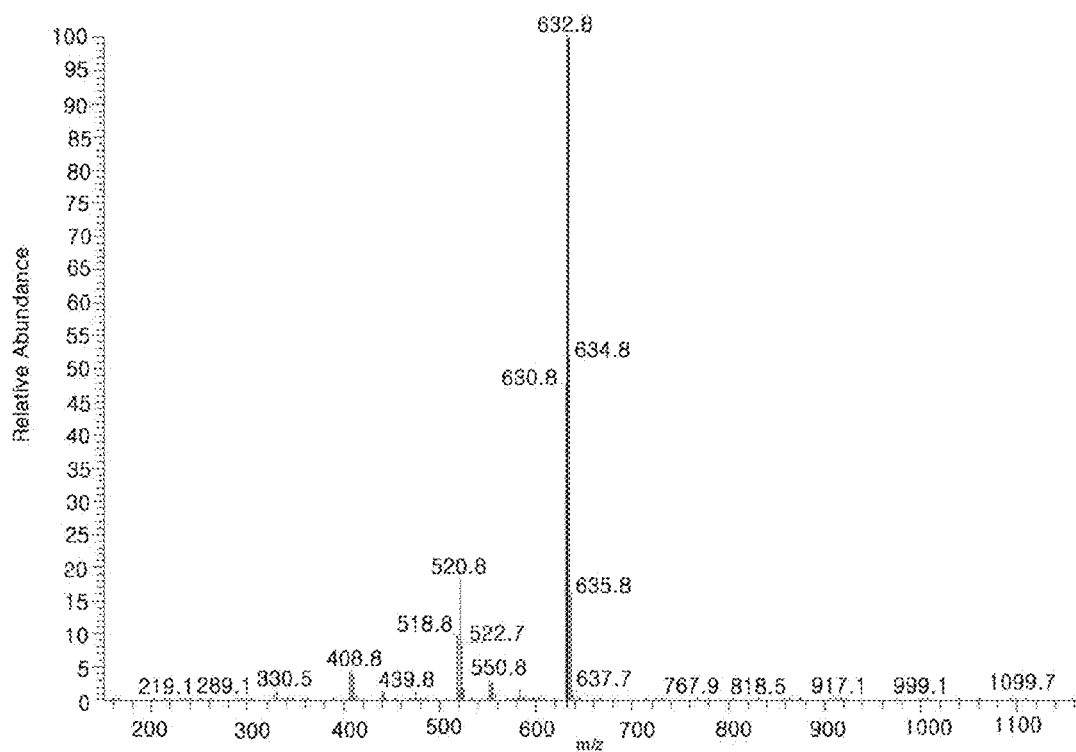
FIG. 12 shows the MS spectrum of 4-bromo-7-(5-bromothiophen-2-yl)-5,6-bis(octyloxy)benzo[c]-1,2,5-thiadiazole synthesized in Preparation Example 1-E.

FIG. 12 shows the MS spectrum of 4-bromo-7-(5-bromothiophen-2-yl)-5,6-bis(octyloxy)benzo[c]-1,2,5-thiadiazole prepared in Preparation Example 1-D.

Preparation Example 2

Preparation of polymer (poly(N-9-heptadecanylcarbazole-alt-4-(thiophen-2-yl)-2,1,3,-benzothiadiazole)

Preparation Example 2

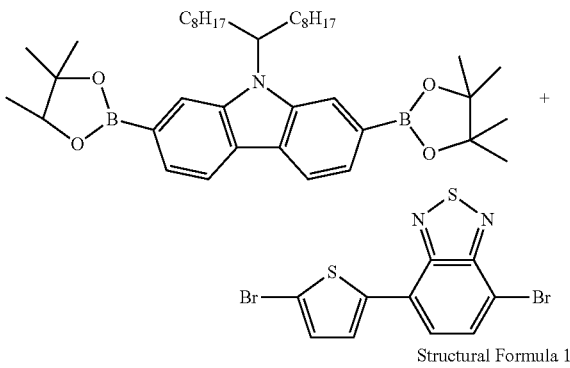

Structural Formula 1

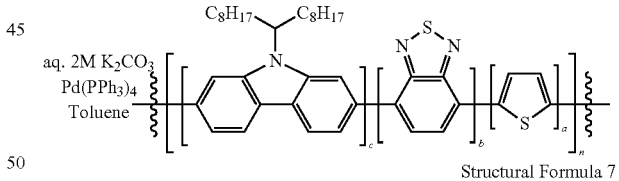

Structural Formula 7

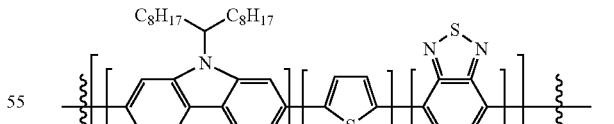

In this Example, 2,7-bis(4,4,5,5-tetramethyl-1,3,2-dioxaborolan-2-yl)-N,9-heptadecanylcarbazole was prepared with reference to the literature (N. Blouin, A. Michaud, M. Leclerc, Adv. Mater. 19, 2007, 2295-2300).

2,7-bis(4,4,5,5-tetramethyl-1,3,2-dioxaborolan-2-yl)-N,9-heptadecanylcarbazole (200 mg, 0.304 mmol), 4-bromo-7-(5-bromothiophen-yl)-2,1,3-benzothiadiazole (114 mg, 0.304 mmol), 2M potassium carbonate aqueous solution (5 ml) and Pd(PPh$_3$)$_4$ (5 mg) were added to and dissolved in 10 ml of toluene and stirred under reflux. After 72 hours, the mixture was cooled to room temperature, and methanol was added thereto. The solid was filtered and Soxhlet-extracted with acetone, hexane and chloroform. The extract was precipitated in methanol, and the solid was filtered.

Yield: 51%.

Number-average molecular weight: 32,100 g/mol.

Weight-average molecular weight: 58,200 g/mol.

Figure 4:
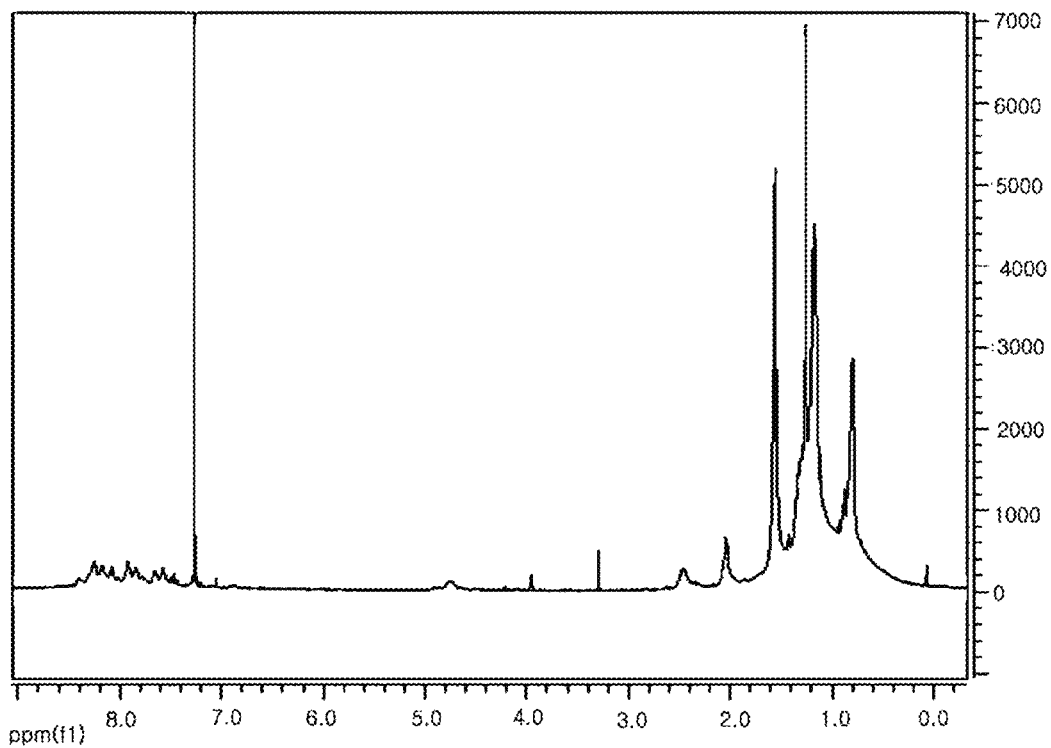
FIG. 4 shows the NMR spectrum of poly(N-9-heptadecanylcarbazole-alt-4-(thiophen-2-yl)-2,1,3-benzothiadiazole) prepared in Preparation Example 2.
Figure 5:
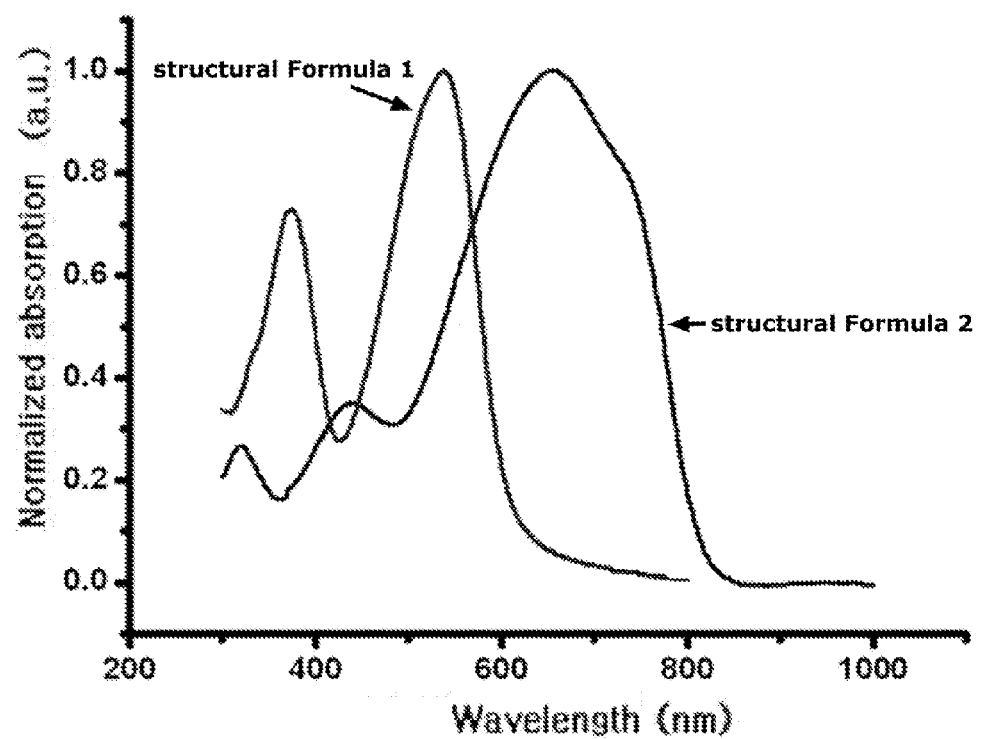
FIG. 5 shows the UV absorbance spectra of films formed from compounds having the structural formulas 1 and 2.

FIG. 4 shows the NMR spectrum of the poly(N-9-heptadecanylcarbazole-alt-4-(thiophen-2-yl)-2,1,3,-benzothiadiazole prepared in Preparation Example 2.

Preparation Example 3

Preparation of polymer (poly(4,4'-bis(2-ethylhexyl) dithieno[3,2-b:2',3'-d]silole-alt-4-(thiophen-2-yl)2,1, 3-benzothiadiazole)

Preparation Example 3

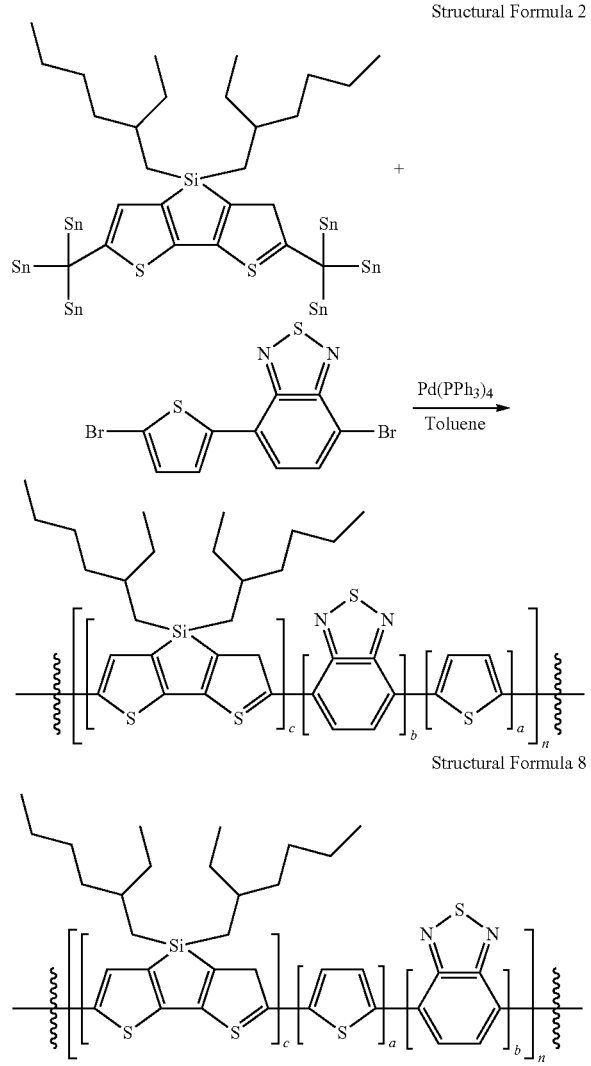

Structural Formula 2

Structural Formula 8

In this Example, 4,4'-bis(2-ethylhexyl)-5,5'-bis(trimethyltin)dithieno[3,2-b:2',3'-d]silole was prepared with reference to the reference (L. Hou, J. Hou, H. Y. Chen, S. Zhang, Y. Jiang, T. L. Chen, Y. Yang, Macromolecules 42, 2009, 6564-6571).

4,4'-bis(2-ethylhexyl)-5,5'-bis(trimethyltin)dithieno[3,2-b:2',3'-d]silole (1.15 g, 1.55 mmol), 4-bromo-7-(5-bromothiophen-yl)-2,1,3-benzothiadiazole (583 mg, 1.55 mmol), and Pd(PPh$_3$)$_4$ (25 mg) were added to and dissolved in 40 ml of toluene and stirred under reflux. After hours, the mixture was cooled to room temperature, and methanol was added thereto. The solid was filtered and Soxhlet-extracted with acetone, hexane and chloroform. The extract was precipitated in methanol, and the solid was filtered.

Yield: 65%.

Number-average molecular weight: 12,400 g/mol.

Weight-average molecular weight: 39,100 g/mol.

Figure 6:
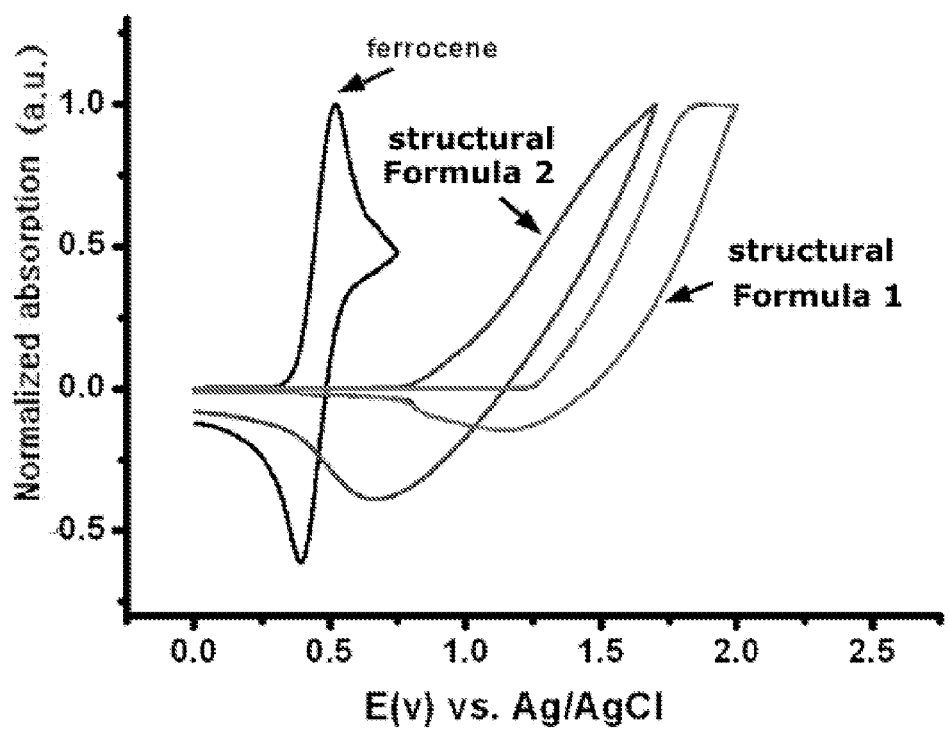
FIG. 6 shows the cyclic voltammetry of compounds having the structural formulas 1 and 2.

FIG. 6 shows the UV absorbance spectra of films formed from the compounds of structural formulas 1 and 2. To measure the UV absorbance spectra, each of the polymers was dissolved in chlorobenzene at a concentration of 1 wt % to prepare solutions, and each of the solutions was spin-coated on a glass substrate to prepare samples.

Figure 7:
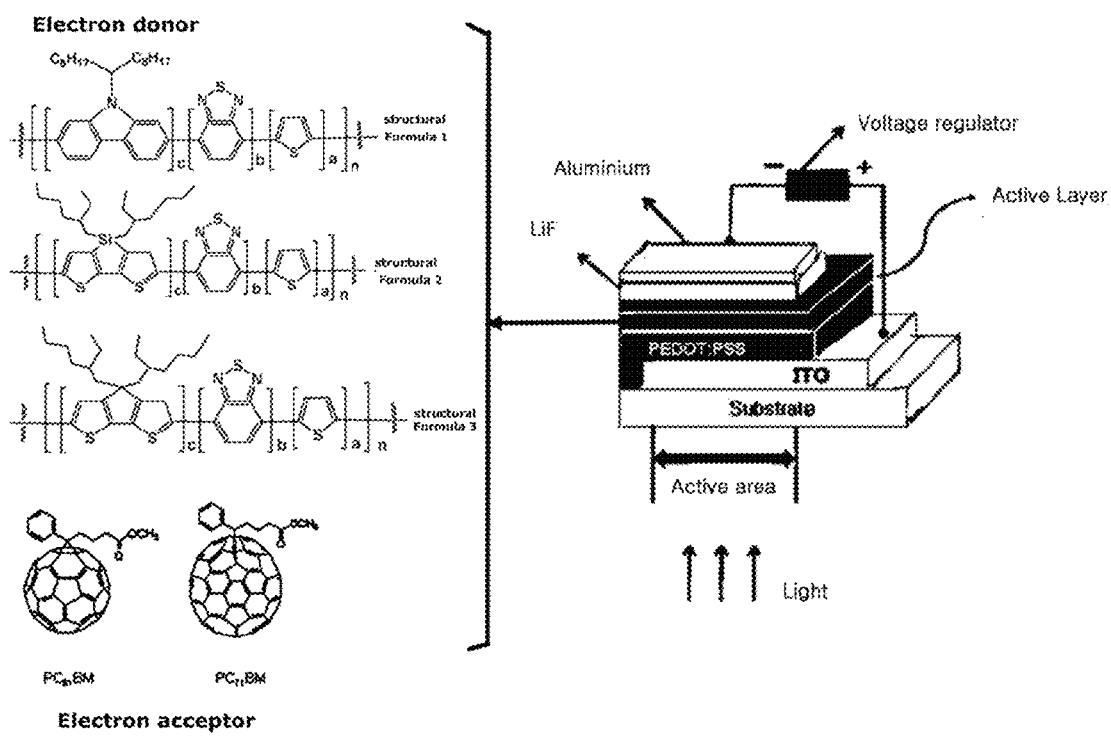
FIG. 7 shows an organic solar cell comprising the compound of structural formula 1 or 2 together with $PC_{61}BM$ or $PC_{71}BM$.

FIG. 7 shows the cyclic voltammetry of the compounds of structural formulas 1 and 2. To measure the cyclic voltammetry, each of the polymer solutions was drop-casted on a working electrode to prepare films. The cyclic voltammetry of the films was measured using an electrolyte obtained by dissolving 0.1M B Bu$_4$NBF$_4$ in acetonitrile at a concentration of 0.1M, a working electrode made of glassy carbon, a reference electrode made of Ag/AgCl, and a counter electrode made of Pt.

Preparation Example 4

Preparation of polymer (poly(N-9-heptadecanylcarbazole-alt-4-(thiophen-2-yl) 5,6-bis(octyloxy)benzo[c]-1,2,5-thiadiazole)

Preparation Example 4

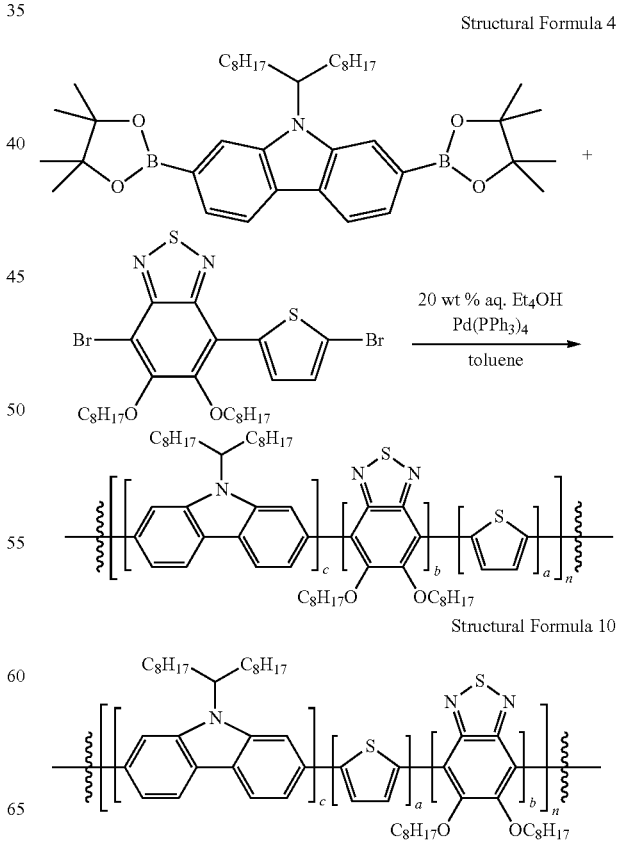

Structural Formula 4

Structural Formula 10

In this Example, 2,7-bis(4,4,5,5-tetramethyl-1,3,2-dioxaborolan-2-yl)-N,9-heptadecanylcarbazole was prepared with reference to the literature (N. Blouin, A. Michaud, M. Leclerc, Adv. Mater. 19, 2007, 2295-2300).

2,7-bis(4,4,5,5-tetramethyl-1,3,2-dioxaborolan-2-yl)-N,9-heptadecanylcarbazole (416 mg, 0.632 mmol), 4-bromo-7-(5-bromothiophen-2-yl)-5,6-bis(octyloxy)benzo[c]-1,2,5-thiadiazole (400 mg, 0.632 mmol), 20 wt % Et$_4$NOH aqueous solution (6 ml) and Pd(PPh$_3$)$_4$ (22 mg) were added to and dissolved in 10 ml of toluene and stirred under reflux. After 72 hours, the mixture was cooled to room temperature, and methanol was added thereto. The solid was filtered and Soxhlet-extracted with acetone, hexane and chloroform. The extract was precipitated in methanol, and the solid was filtered.

Yield: 50%.

Number-average molecular weight: 60,700 g/mol.

Weight-average molecular weight: 110,500 g/mol.

Figure 13:
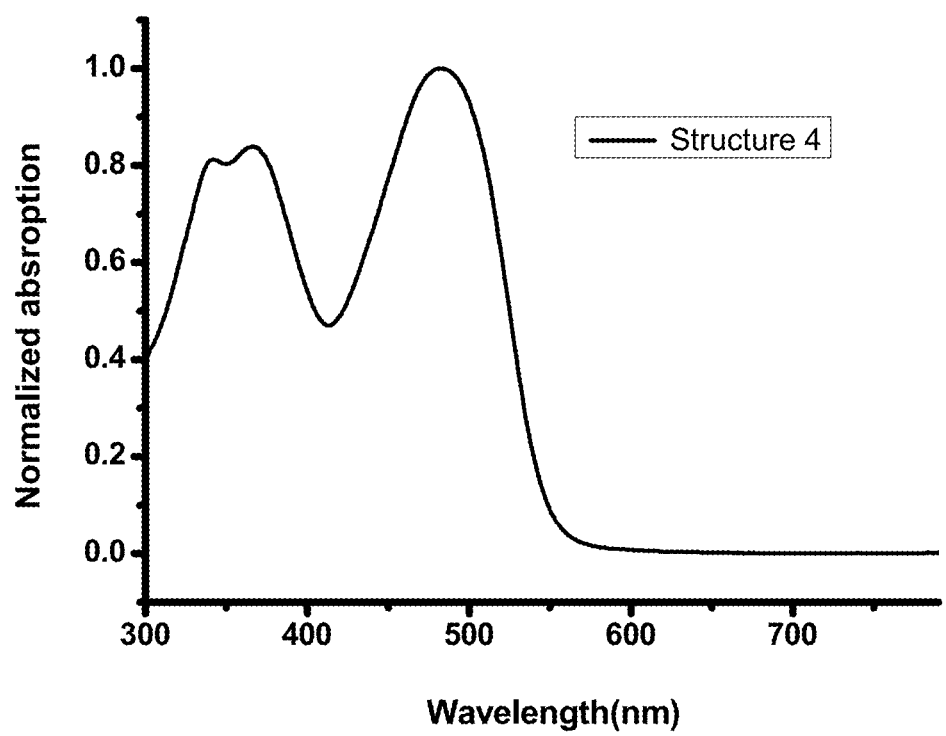
FIG. 13 shows the UV absorbance spectrum of a film formed from the compound of structural formula 4.

FIG. 13 shows the UV absorbance spectrum of a film formed from the compound of structural formula 4. To measure the UV absorbance spectrum, the polymer was dissolved in chlorobenzene at a concentration of 1 wt % to prepare a solution which was then spin-coated on a glass substrate to prepare a sample.

Figure 14:
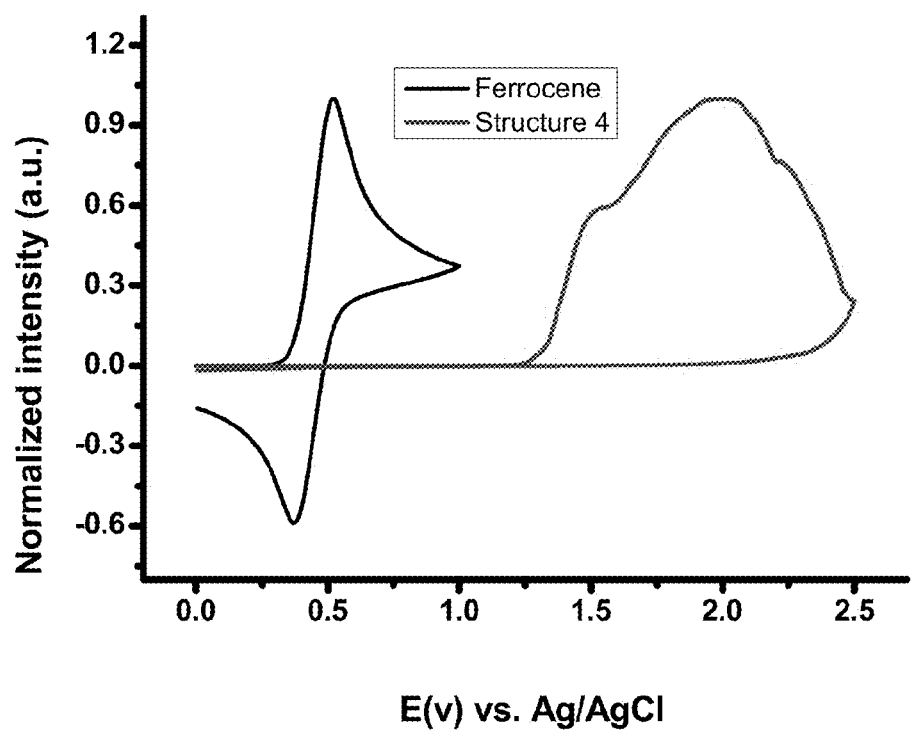
FIG. 14 shows the cyclic voltammetry of the compound of structural formula 4.

FIG. 14 shows the cyclic voltammetry of the compound of structural formula 4. To measure the cyclic voltammetry, the polymer solution was drop-casted on a working electrode to prepare films. The cyclic voltammetry of the film was measured using an electrolyte obtained by dissolving 0.1M B Bu$_4$NBF$_4$ in acetonitrile at a concentration of 0.1M, a working electrode made of glassy carbon, a reference electrode made of Ag/AgCl, and a counter electrode made of Pt.

Preparation Example 5

Preparation of polymer (poly(4,8-bis(2-ethylhexyloxy)benzo[1,2-b:4,5-b']dithiophene-2,6-diyl-alt-4-(thiophene-2-yl)5,6-bis(octyloxy)benzo[c]-1,2,5-thiadiazole)

Preparation Example 5

Structural Formula 5

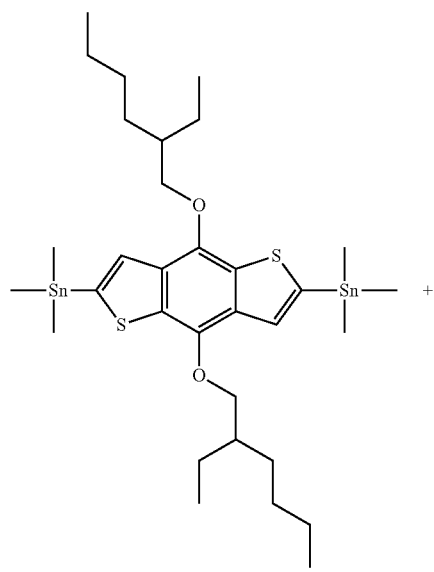

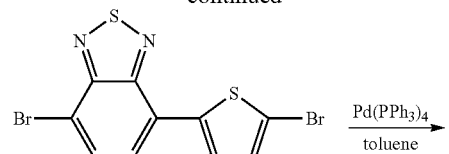

Structural Formula 11

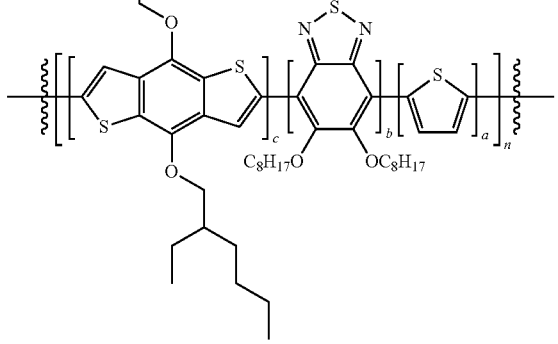

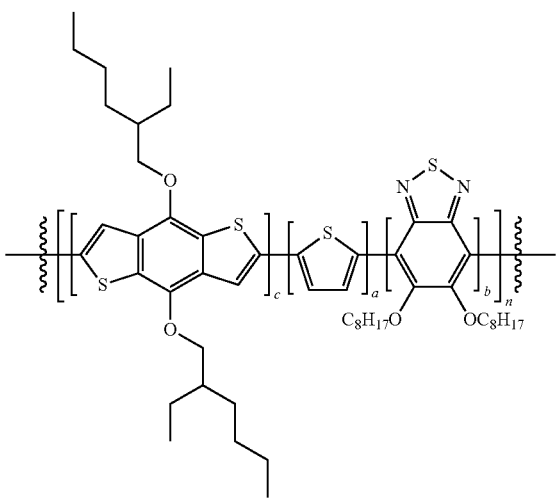

In this Example, 2,6-bis(trimethyltin)-4,8-bis(2-ethylhexyloxy)benzo[1,2-b:4,5-b']dithiophene was prepared with reference to the literature (P. Morvillo, F. Parenti, R. Diana, C. Fontanesi, A. Mucci, F. Tassinari, L. Schenetti, Solar Energy Materials & Solar Cells 104, 2012, 45-52).

2,6-Bis(trimethyltin)-4,8-bis(2-ethylhexyloxy)benzo[1,2-b:4,5-b']dithiophene (488 mg, 0.632 mmol), 4-bromo-7-(5-bromothiophen-2-yl)-5,6-bis(octyloxy)benzo[c]-1,2,5-thiadiazole (400 mg, 0.632 mmol) and Pd(PPh$_3$)$_4$ (22 mg) were added to and dissolved in 10 ml of toluene and stirred under reflux. After hours, the mixture was cooled to room temperature, and methanol was added thereto. The solid was filtered and Soxhlet-extracted with acetone, hexane and chloroform. The extract was precipitated in methanol, and the solid was filtered.

Yield: 40%.

Number-average molecular weight: 39,500 g/mol.

Weight-average molecular weight: 64,000 g/mol.

Figure 16:
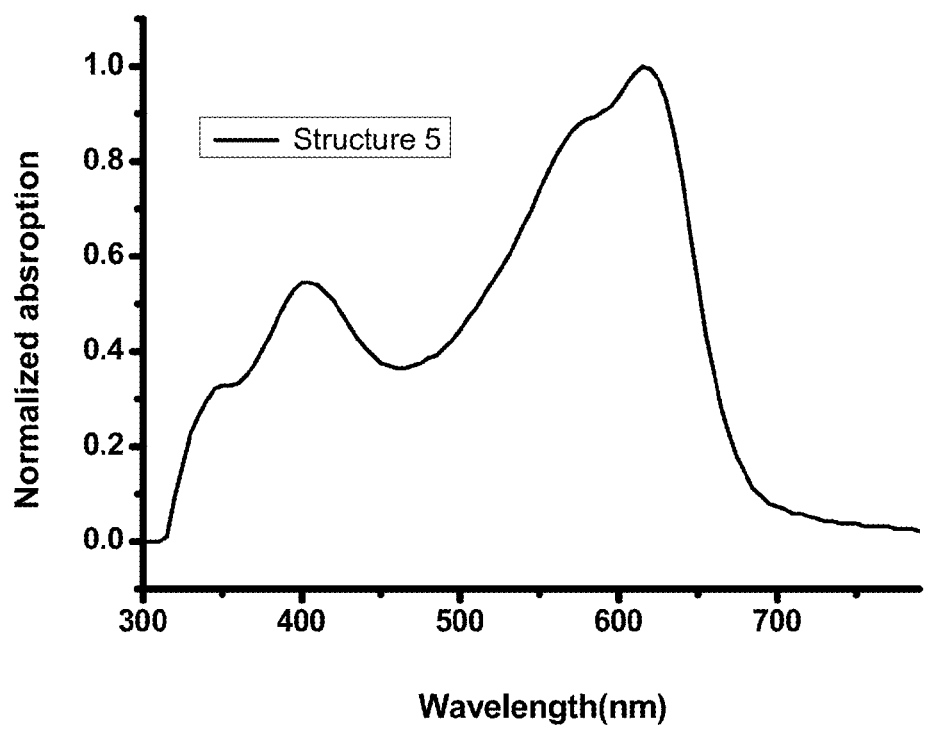
FIG. 16 shows the UV absorbance spectrum of a film formed from the compound of structural formula 5.

FIG. 16 shows the UV absorbance spectrum of a film formed from the compound of structural formula 5. To measure the UV absorbance spectrum, the polymer was dissolved in chlorobenzene at a concentration of 1 wt % to prepare a solution which was then spin-coated on a glass substrate to prepare a sample.

Figure 17:
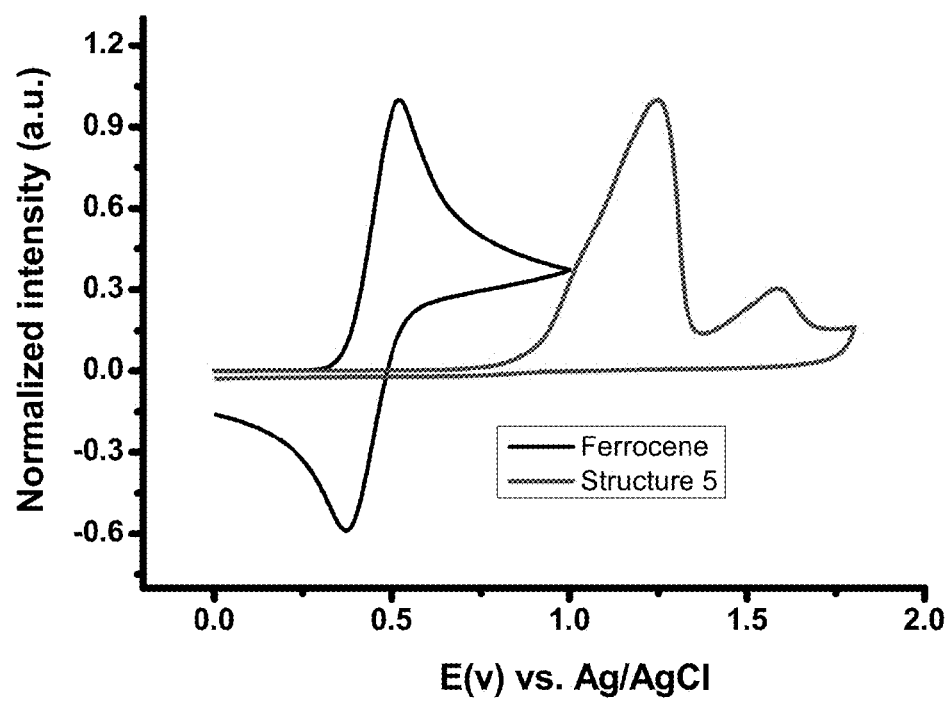
FIG. 17 shows the cyclic voltammetry of the compound of structural formula 5.

FIG. 17 shows the cyclic voltammetry of the compound of structural formula 5. To measure the cyclic voltammetry, the polymer solution was drop-casted on a working electrode to prepare films. The cyclic voltammetry of the film was measured using an electrolyte obtained by dissolving 0.1M B Bu$_4$NBF$_4$ in acetonitrile at a concentration of 0.1M, a working electrode made of glassy carbon, a reference electrode made of Ag/AgCl, and a counter electrode made of Pt.

Preparation Example 6

Preparation of polymer (poly(thiophene-2,5-yl)-alt-4-(thiophene-2-yl) 5,6-bis(octyloxy)benzo[c]-1,2,5-thiadiazole)

Preparation Example 6

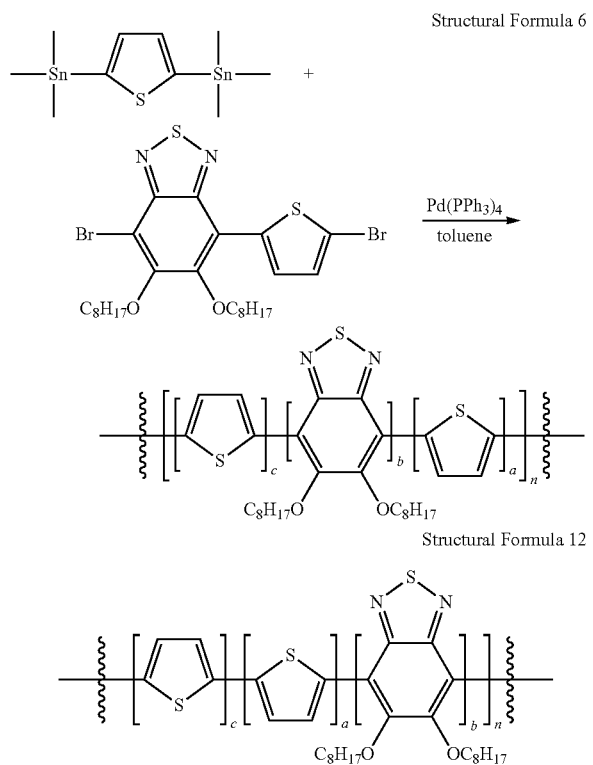

2,5-Bis(trimethylstannyl)thiophene (259 mg, 0.632 mmol), 4-bromo-7-(5-bromothiophen-2-yl)-5,6-bis(octyloxy)benzo[c]-1,2,5-thiadiazole (400 mg, 0.632 mmol) and Pd(PPh$_3$)$_4$ (22 mg) were added to and dissolved in 10 ml of toluene and stirred under reflux. After 72 hours, the mixture was cooled to room temperature, and methanol was added thereto. The solid was filtered and Soxhlet-extracted with acetone, hexane and chloroform. The extract was precipitated in methanol, and the solid was filtered.

Yield: 53%.
Number-average molecular weight: 22,500 g/mol.
Weight-average molecular weight: 58,000 g/mol.

Figure 19:
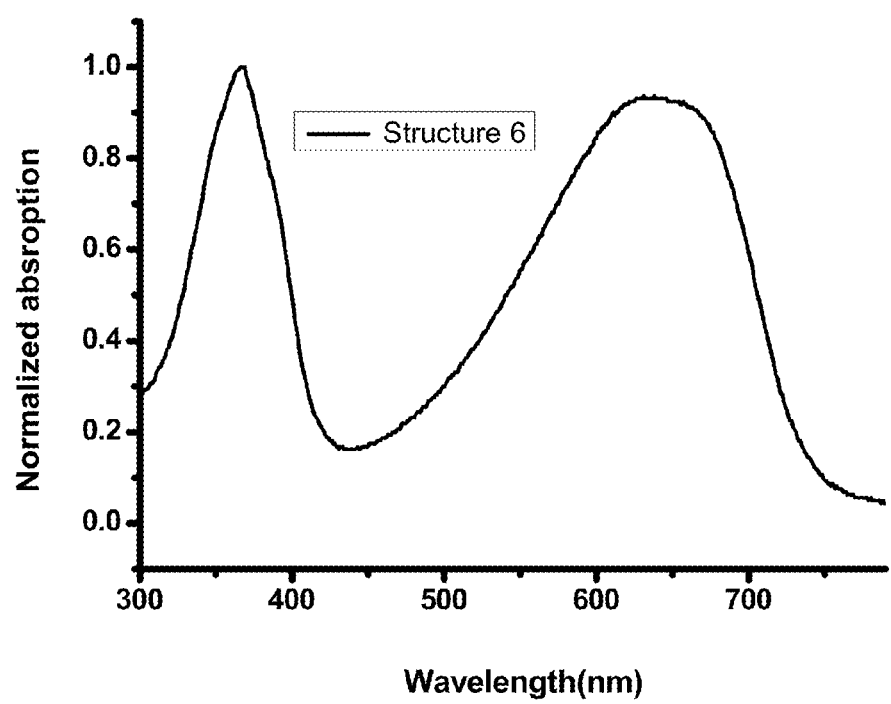
FIG. 19 shows the UV absorbance spectrum of a film formed from the compound of structural formula 6.
Figure 20:
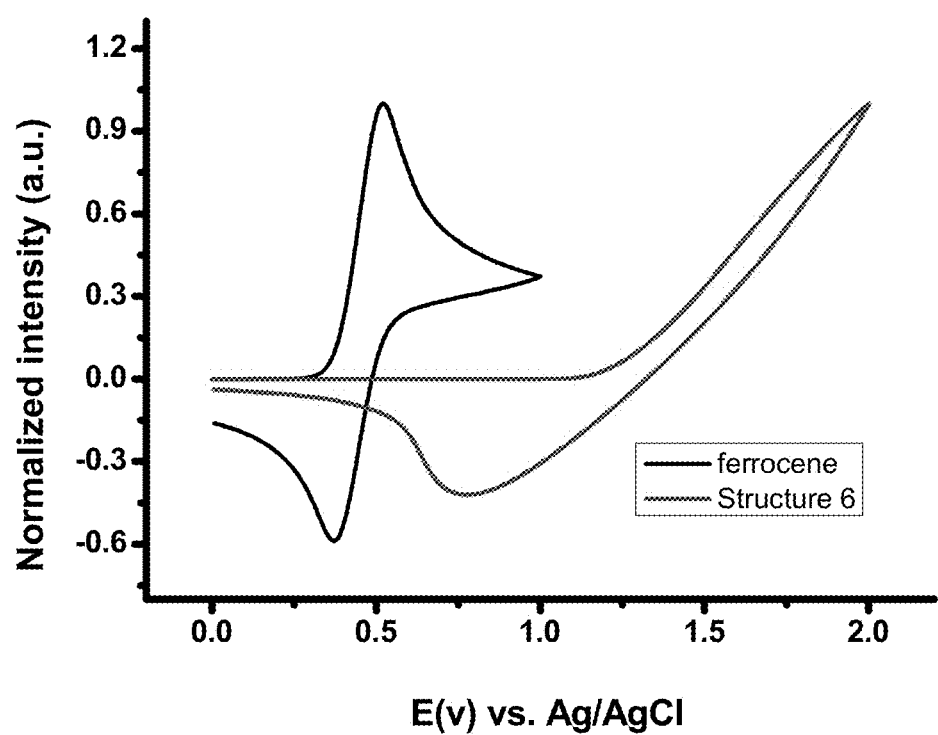
FIG. 20 shows the cyclic voltammetry of the compound of structural formula 6.

FIG. 19 shows the UV absorbance spectrum of a film formed from the compound of structural formula 6. To measure the UV absorbance spectrum, the polymer was dissolved in chlorobenzene at a concentration of 1 wt % to prepare a solution which was then spin-coated on a glass substrate to prepare a sample.

FIG. 10 shows the cyclic voltammetry of the compound of structural formula 6. To measure the cyclic voltammetry, the polymer solution was drop-casted on a working electrode to prepare films. The cyclic voltammetry of the film was measured using an electrolyte obtained by dissolving 0.1M B Bu$_4$NBF$_4$ in acetonitrile at a concentration of 0.1M, a working electrode made of glassy carbon, a reference electrode made of Ag/AgCl, and a counter electrode made of Pt.

Example 1

Fabrication of Organic Solar Cell

The polymer prepared in Preparation Example 2 was mixed with PC$_{61}$BM at a ratio of 1:4, and the mixture was dissolved in 1,2-dichlorobenzene (DCB) at a concentration of 1.0-2.0 wt % to prepare a composite solution. An organic solar cell having a structure of ITO/PEDOT:PSS/photoactive layer/LiF/Al was fabricated in the following manner. An ITO-coated glass substrate was ultrasonically washed with distilled water, acetone and 2-propanol, and the ITO surface was treated with ozone for 10 minutes, spin-coated with PEDOT:PSS (baytrom P), and heat-treated at 120° C. for 10 minutes. To form a photoactive layer, the polymer-PCBM composite solution was filtered through a 0.45-μm PP syringe filter, after which it was spin-coated on the substrate and heat-treated at 120° C. for 5 minutes. Then, LiF was deposited on the substrate to a thickness of 7 Å under a vacuum of 3×10$^{-8}$ torr using a thermal evaporator, followed by deposition of Al to a thickness of 200 nm.

Example 2

Fabrication of Organic Solar Cell

The polymer prepared in Preparation Example 2 was mixed with PC$_{71}$BM at a ratio of 1:4, and the mixture was dissolved in 1,2-dichlorobenzene (DCB) at a concentration of 1.0-2.0 wt % to prepare a composite solution. An organic solar cell having a structure of ITO/PEDOT:PSS/photoactive layer/LiF/Al was fabricated in the following manner. An ITO-coated glass substrate was ultrasonically washed with distilled water, acetone and 2-propanol, and the ITO surface was treated with ozone for 10 minutes, spin-coated with PEDOT:PSS (baytrom P), and heat-treated at 120° C. for 10 minutes. To form a photoactive layer, the polymer-PCBM composite solution was filtered through a 0.45-μm PP syringe filter, after which it was spin-coated on the substrate and heat-treated at 120° C. for minutes. Then, LiF was deposited on the substrate to a thickness of 7 Å under a vacuum of 3×10$^{-8}$ torr using a thermal evaporator, followed by deposition of Al to a thickness of 200 nm.

Example 3

Fabrication of Organic Solar Cell

The polymer prepared in Preparation Example 3 was mixed with PC$_{61}$BM at a ratio of 1:4, and the mixture was dissolved in 1,2-dichlorobenzene (DCB) at a concentration of 1.0-2.0 wt % to prepare a composite solution. An organic solar cell having a structure of ITO/PEDOT:PSS/photoactive layer/LiF/Al was fabricated in the following manner. An ITO-coated glass substrate was ultrasonically washed with distilled water, acetone and 2-propanol, and the ITO surface was treated with ozone for 10 minutes, spin-coated with PEDOT:PSS (baytrom P), and heat-treated at 120° C. for 10 minutes. To form a photoactive layer, the polymer-PCBM composite solution was filtered through a 0.45-μm PP syringe filter, after which it was spin-coated on the substrate and heat-treated at 120° C. for 5 minutes. Then, LiF was deposited on the substrate to a thickness of 7 Å under a vacuum of $3\times10^{-8}$ torr using a thermal evaporator, followed by deposition of Al to a thickness of 200 nm.

Example 4

Fabrication of Organic Solar Cell

The polymer prepared in Preparation Example 3 was mixed with $PC_{71}BM$ at a ratio of 1:4, and the mixture was dissolved in 1,2-dichlorobenzene (DCB) at a concentration of 1.0-2.0 wt % to prepare a composite solution. An organic solar cell having a structure of ITO/PEDOT:PSS/photoactive layer/LiF/Al was fabricated in the following manner. An ITO-coated glass substrate was ultrasonically washed with distilled water, acetone and 2-propanol, and the ITO surface was treated with ozone for 10 minutes, spin-coated with PEDOT:PSS (baytrom P), and heat-treated at 120° C. for 10 minutes. To form a photoactive layer, the polymer-PCBM composite solution was filtered through a 0.45-μm PP syringe filter, after which it was spin-coated on the substrate and heat-treated at 120° C. for 5 minutes. Then, LiF was deposited on the substrate to a thickness of 7 Å under a vacuum of $3\times10^{-8}$ torr using a thermal evaporator, followed by deposition of Al to a thickness of 200 nm.

Example 5

Fabrication of Organic Solar Cell

The polymer prepared in Preparation Example 4 was mixed with $PC_{61}BM$ at a ratio of 1:4, and the mixture was dissolved in 1,2-dichlorobenzene (DCB) at a concentration of 1.0-2.0 wt % to prepare a composite solution. An organic solar cell having a structure of ITO/PEDOT:PSS/photoactive layer/LiF/Al was fabricated in the following manner. An ITO-coated glass substrate was ultrasonically washed with distilled water, acetone and 2-propanol, and the ITO surface was treated with ozone for 10 minutes, spin-coated with PEDOT:PSS (baytrom P), and heat-treated at 120° C. for 10 minutes. To form a photoactive layer, the polymer-PCBM composite solution was filtered through a 0.45-μm PP syringe filter, after which it was spin-coated on the substrate and heat-treated at 120° C. for 5 minutes. Then, LiF was deposited on the substrate to a thickness of 7 Å under a vacuum of $3\times10^{-8}$ torr using a thermal evaporator, followed by deposition of Al to a thickness of 200 nm.

Example 6

Fabrication of Organic Solar Cell

The polymer prepared in Preparation Example 5 was mixed with $PC_{61}BM$ at a ratio of 1:4, and the mixture was dissolved in 1,2-dichlorobenzene (DCB) at a concentration of 1.0-2.0 wt % to prepare a composite solution. An organic solar cell having a structure of ITO/PEDOT:PSS/photoactive layer/LiF/Al was fabricated in the following manner. An ITO-coated glass substrate was ultrasonically washed with distilled water, acetone and 2-propanol, and the ITO surface was treated with ozone for 10 minutes, spin-coated with PEDOT:PSS (baytrom P), and heat-treated at 120° C. for 10 minutes. To form a photoactive layer, the polymer-PCBM composite solution was filtered through a 0.45-μm PP syringe filter, after which it was spin-coated on the substrate and heat-treated at 120° C. for 5 minutes. Then, LiF was deposited on the substrate to a thickness of 7 Å under a vacuum of $3\times10^{-8}$ torr using a thermal evaporator, followed by deposition of Al to a thickness of 200 nm.

Example 7

Fabrication of Organic Solar Cell

The polymer prepared in Preparation Example 6 was mixed with $PC_{61}BM$ at a ratio of 1:4, and the mixture was dissolved in 1,2-dichlorobenzene (DCB) at a concentration of 1.0-2.0 wt % to prepare a composite solution. An organic solar cell having a structure of ITO/PEDOT:PSS/photoactive layer/LiF/Al was fabricated in the following manner. An ITO-coated glass substrate was ultrasonically washed with distilled water, acetone and 2-propanol, and the ITO surface was treated with ozone for 10 minutes, spin-coated with PEDOT:PSS (baytrom P), and heat-treated at 120° C. for 10 minutes. To form a photoactive layer, the polymer-PCBM composite solution was filtered through a 0.45-μm PP syringe filter, after which it was spin-coated on the substrate and heat-treated at 120° C. for 5 minutes. Then, LiF was deposited on the substrate to a thickness of 7 Å under a vacuum of $3\times10^{-8}$ torr using a thermal evaporator, followed by deposition of Al to a thickness of 200 nm.

Comparative Example 1

Fabrication of Organic Solar Cell

P3HT (poly(3-hexylthiophene)) was mixed with $PC_{61}BM$ at a ratio of 1:1, and the mixture was dissolved in 1,2-dichlorobenzene (DCB) at a concentration of 1.0-2.0 wt % to prepare a composite solution. An organic solar cell having a structure of ITO/PEDOT:PSS/photoactive layer/LiF/Al was fabricated in the following manner. An ITO-coated glass substrate was ultrasonically washed with distilled water, acetone and 2-propanol, and the ITO surface was treated with ozone for 10 minutes, spin-coated with PEDOT:PSS (baytrom P), and heat-treated at 120° C. for 10 minutes. To form a photoactive layer, the polymer-PCBM composite solution was filtered through a 0.45-μm PP syringe filter, after which it was spin-coated on the substrate and heat-treated at 120° C. for 5 minutes. Then, LiF was deposited on the substrate to a thickness of 7 Å under a vacuum of $3\times10^{-8}$ torr using a thermal evaporator, followed by deposition of Al to a thickness of 200 nm.

Comparative Example 2

Fabrication of Organic Solar Cell

P3HT (poly(3-hexylthiophene)) was mixed with $PC_{71}BM$ at a ratio of 1:1, and the mixture was dissolved in 1,2-dichlorobenzene (DCB) at a concentration of 1.0-2.0 wt % to prepare a composite solution. An organic solar cell having a structure of ITO/PEDOT:PSS/photoactive layer/LiF/Al was fabricated in the following manner. An ITO-coated glass substrate was ultrasonically washed with distilled water, acetone and 2-propanol, and the ITO surface was treated with ozone for 10 minutes, spin-coated with PEDOT:PSS (baytrom P), and heat-treated at 120° C. for 10 minutes. To form a photoactive layer, the polymer-PCBM composite solution was filtered through a 0.45-μm PP syringe filter, after which it was spin-coated on the substrate and heat-treated at 120° C. for 5 minutes. Then, LiF was deposited on the substrate to a thickness of 7 Å under a vacuum of 3×10⁻⁸ torr using a thermal evaporator, followed by deposition of Al to a thickness of 200 nm.

Test Example 1

Test for Organic Solar Cells

The photovoltaic properties of the organic solar cells fabricated in Examples 1 to 7 and Comparative Examples 1 and 2 were measured under a condition of 100 mW/cm² (AM 1.5), and the results of the measurement are shown in Table 1 below.

TABLE 1

| | Photoactive layer | Total thickness (nm) | Open circuit voltage $V_{OC}$ (V) | Short-circuit current $J_{SC}$ (mA/cm²) | Fill factor FF | Photovoltaic conversion efficiency PCE (%) |
|---|---|---|---|---|---|---|
| Example 1 | Structural formula 1/PC₆₁BM = 1:4 | 71 | 0.75 | 7.16 | 0.48 | 2.41 |
| Example 2 | Structural formula 1/PC₇₁BM = 1:4 | 92 | 0.80 | 7.3 | 0.51 | 2.96 |
| Example 3 | Structural formula 2/PC₆₁BM = 1:4 | 65 | 0.86 | 8.1 | 60.3 | 4.3 |
| Example 4 | Structural formula 2/PC₇₁BM = 1:4 | 65 | 0.87 | 8.3 | 58.6 | 4.3 |
| Example 5 | Structural formula 4/PC₆₁BM = 1:4 | 87 | 0.90 | 1.9 | 30.8 | 0.54 |
| Example 6 | Structural formula 5/PC₆₁BM = 1:4 | 74 | 0.80 | 7.1 | 62.6 | 3.6 |
| Example 7 | Structural formula 6/PC₆₁BM = 1:4 | 81 | 0.61 | 3.7 | 37.1 | 0.84 |
| Comparative Example 1 | P3HT/PC₆₁BM = 1:1 | 90 | 0.72 | 8.3 | 45.5 | 2.8 |
| Comparative Example 2 | P3HT/PC₇₁BM = 1:1 | 90 | 0.71 | 8.3 | 55.6 | 3.3 |

FIG. 7 shows the organic solar cell fabricated using the compound of structural formula 1 or 2 together with PC₆₁BM or PC₇₁BM.

Figure 8:
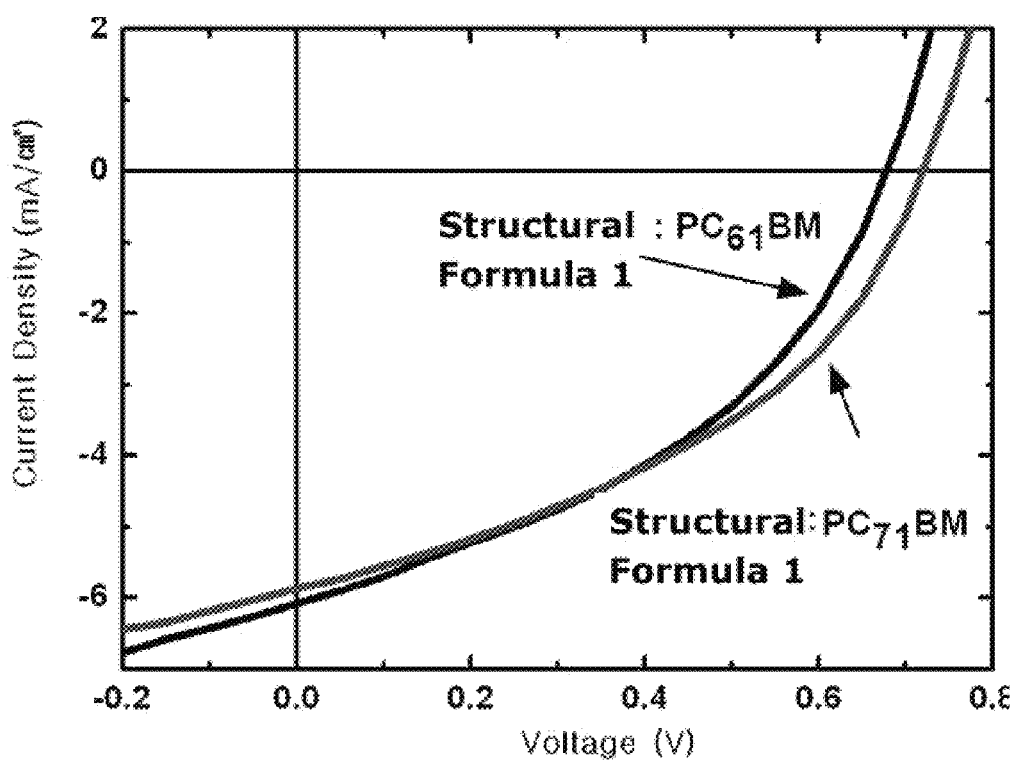
FIG. 8 shows the I-V curves of organic solar cells fabricated in Examples 1 and 2, which comprise poly(N-9-heptadecanylcarbazole-alt-4-(thiophen-2-yl)-2,1,3-benzothiadiazole), which is a compound of structural formula 1.

FIG. 8 shows the I-V curves of the organic solar cells fabricated in Examples 1 and 2, which comprise the poly(N-9-heptadecanylcarbazole-alt-4-(thiophen-2-yl)2,1,3-benzothiazole) prepared in Preparation Example 2.

Figure 9:
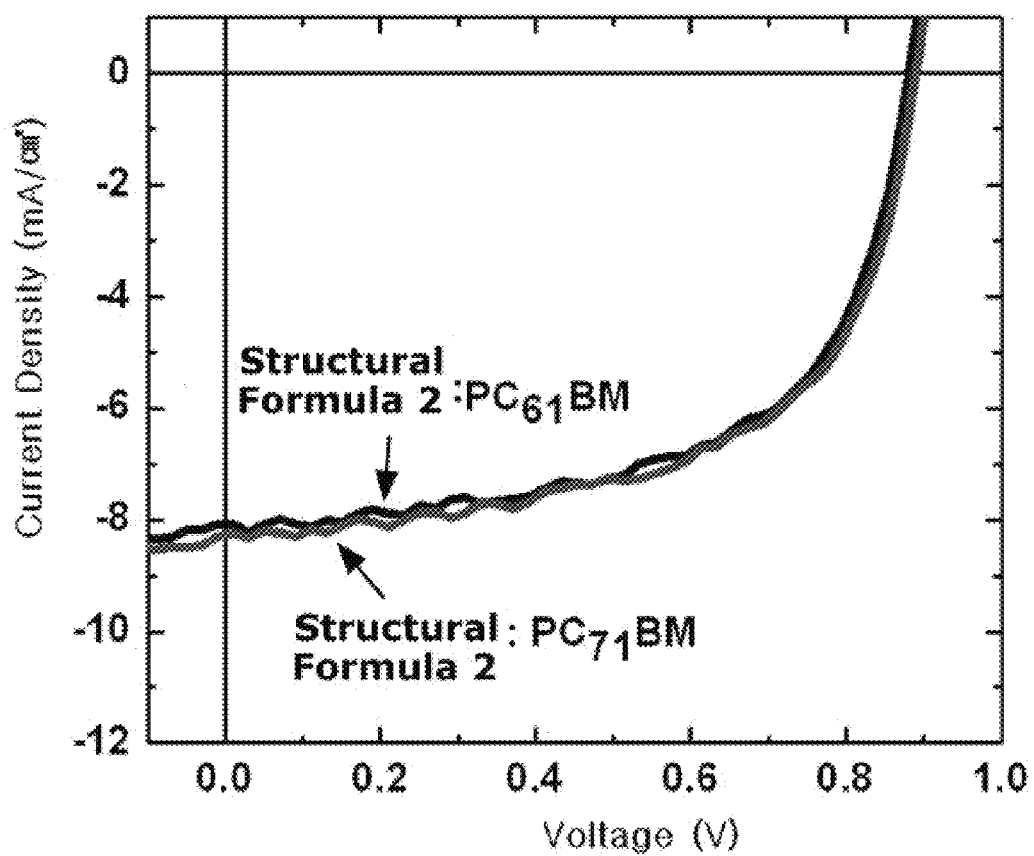
FIG. 9 shows the I-V curves of organic solar cells fabricated in Examples 3 and 4, which comprise poly(4,4'-bis(2-ethylhexyl)dithieno[3,2-b:2',3'-d]silole-alt-4-(thiophen-2-yl)2,1,3-benzothiadiazole), which is a compound of structural formula 2.

FIG. 9 shows the I-V curves of the organic solar cells fabricated in Examples 3 and 4, which comprise the poly(4,4'-bis(2-ethylhexyl)dithieno[3,2-b:2',3'-d]silole-alt-4-(thiophen-2-yl)2,1,3-benzothiadiazole) prepared in Preparation Example 3.

Figure 15:
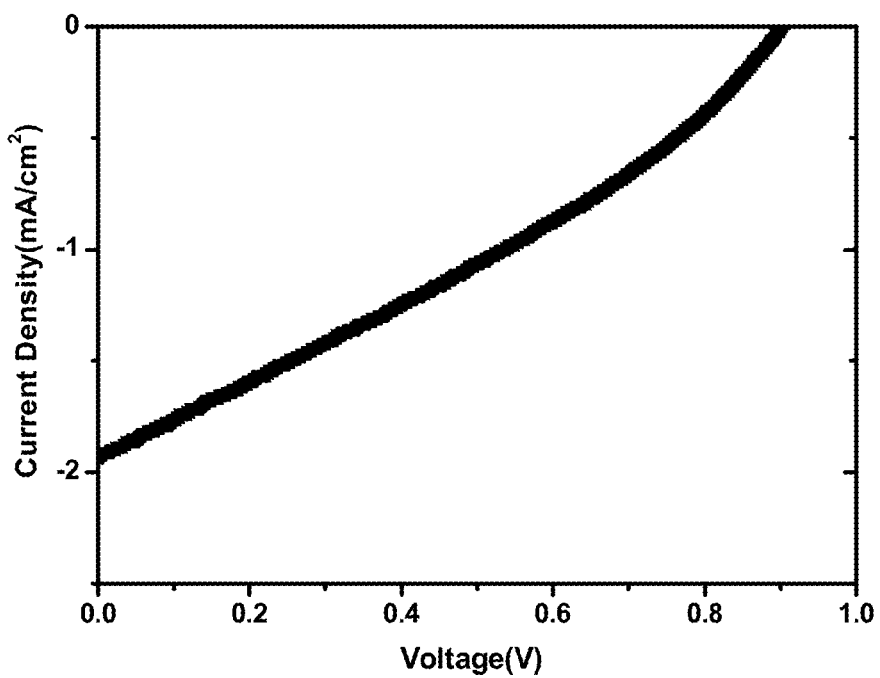
FIG. 15 shows the I-V curve of an organic solar cell fabricated in Example 5, which comprises poly(N-9-heptadecanylcarbazole-alt-4-(thiophen-2-yl)5,6-bis(octyloxy)benzo[c]-1,2,5-thiadiazole), which is the compound of structural formula 4.

FIG. 15 shows the I-V curve of the organic solar cell fabricated in Example 5, which comprises the poly(N-9-heptadecanylcarbazole-alt-4-(thiophen-2-yl)-5,6-bis(octyloxy)benzo[c]-1,2,5-thiadiazole) prepared in Preparation Example 4.

Figure 18:
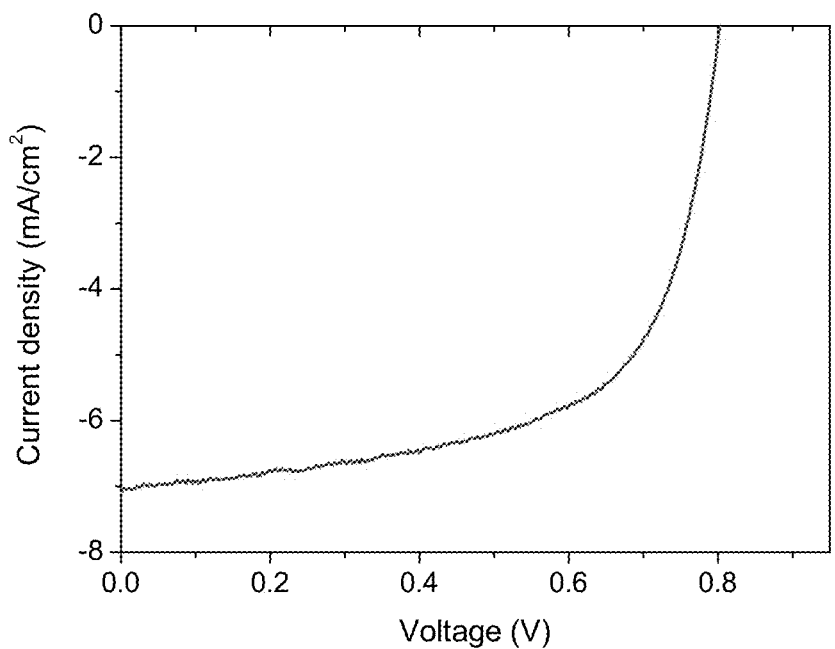
FIG. 18 shows the I-V curve of an organic solar cell fabricated in Example 6, which comprises poly(4,8-bis(2-ethylhexyloxy)benzo[1,2-b:4,5-b']dithiophen-2,6-diyl-alt-4-(thiophen-2-yl)5,6-bis(octyloxy)benzo[c]-1,2,5-thiadiazole), which is the compound of structural formula 5.

FIG. 18 shows the I-V curve of the organic solar cell fabricated in Example 6, which comprises the poly(4,8-bis(2-ethylhexyloxy)benzo[1,2-b:4,5-b']dithiophene-2,6-diyl-alt-4-(thiophen-2-yl)5,6-bis(octyloxy)benzo[c]-1,2,5-thiadiazole) prepared in Preparation Example 5.

Figure 21:
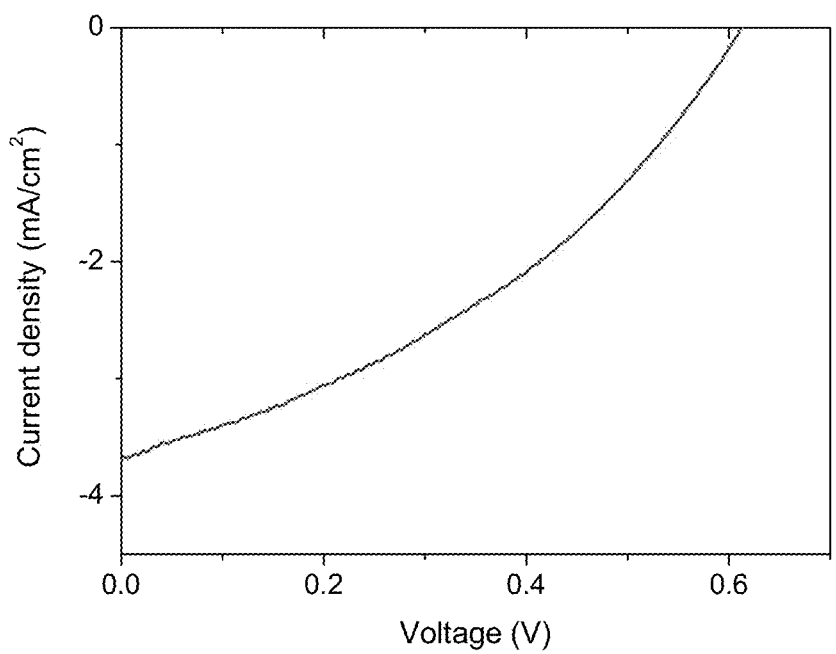
FIG. 21 shows the I-V curve of the organic solar cell fabricated in Example 7, which comprises poly(thiophen-2,5-yl-alt-4-(thiophen-2-yl)5,6-bis(octyloxy)benzo[c]-1,2,5-thiadiazole), which is the compound of structural formula 6.

FIG. 21 shows the I-V curve of the organic solar cell fabricated in Example 7, which comprises the poly(thiophen-2,5-yl-alt-4-(thiophene-2-yl)-5,6-bis(octyloxy)benzo[c]-1,2,5-thiadiazole) prepared in Preparation Example 6.

Although the present disclosure has been described in detail with reference to the specific features, it will be apparent to those skilled in the art that this description is only for a preferred embodiment, and does not limit the scope of the present disclosure. Thus, the substantial scope of the present disclosure will be defined by the appended claims and equivalents thereof.

The invention claimed is:

1. A random polymer comprising a unit of the following chemical formula 14 or 15 and having a number-average molecular weight of 10,000-1,000,000:

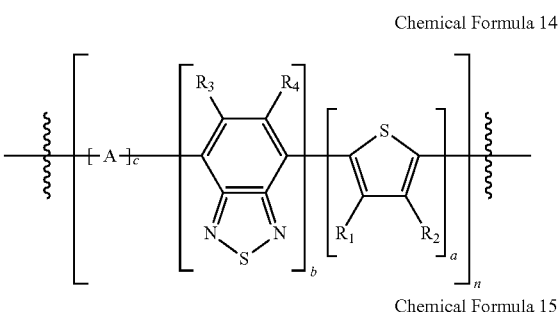

Chemical Formula 14

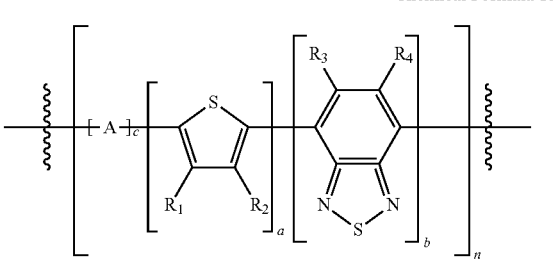

Chemical Formula 15 wherein n is an integer ranging from 2 to 100,000, wherein $R_1$ to $R_4$ are each independently selected from the group consisting of hydrogen; deuterium; a halogen group; a nitro group; a nitrile group; an imide group; an amide group —$CONX_1X_2$, wherein $X_1$ and $X_2$ may be the same or different and are each independently hydrogen, a substituted or unsubstituted $C_{1-25}$ alkyl group or a substituted or unsubstituted $C_{6-25}$ aryl group; a hydroxyl group; an ester group —$COOX_3$, wherein $X_3$ is a substituted or unsubstituted $C_{1-25}$ alkyl group or a substituted or unsubstituted $C_{6-25}$ aryl group; a carbonyl group —$COX_4$, wherein $X_4$ is a substituted or unsubstituted $C_{1-25}$ alkyl group or a substituted or unsubstituted $C_{6-25}$ aryl group; a substituted or unsubstituted $C_{1-25}$ alkyl group; a substituted or unsubstituted $C_{1-25}$ alkoxy group; a substituted or unsubstituted $C_{2-25}$ alkenyl group; a thiophene group unsubstituted or substituted with either a $C_{1-25}$ alkyl group or a $C_{1-25}$ alkoxy group; a selenophene group unsubstituted or substituted with either a $C_{1-25}$ alkyl group or a $C_{1-25}$ alkoxy group; a pyrrole group unsubstituted or substituted with either a $C_{1-25}$ alkyl group or a $C_{1-25}$ alkoxy group; a thiazole group unsubstituted or substituted with either a $C_{1-25}$ alkyl group or a $C_{1-25}$ alkoxy group; an arylamine group unsubstituted or substituted with either a $C_{1-25}$ alkyl group or a $C_{1-25}$ alkoxy group; and an aryl group unsubstituted or substituted with either a $C_{1-25}$ alkyl group or a $C_{1-25}$ alkoxy group;

wherein A is one among structures of the following formulas 5 to 13 or a group in which two or more among structures of the following formulas 5 to 13 are bonded to each other, Chemical Formula 5
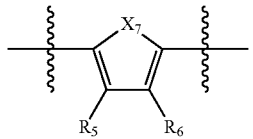

Chemical Formula 6
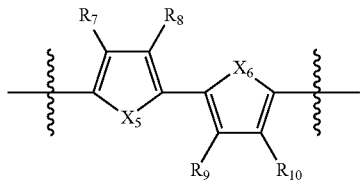

Chemical Formula 7
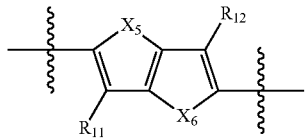

Chemical Formula 8
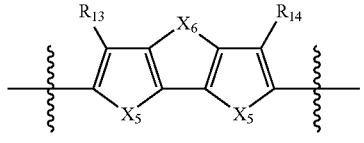

Chemical Formula 9
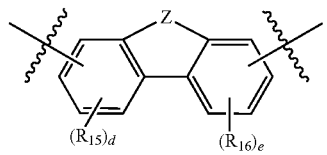

Chemical Formula 10
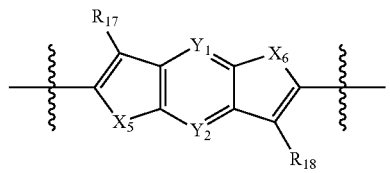

Chemical Formula 11
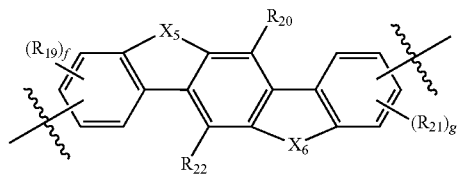

Chemical Formula 12
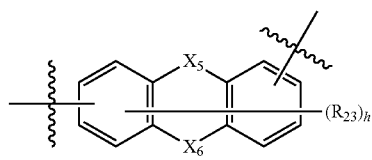

Chemical Formula 13
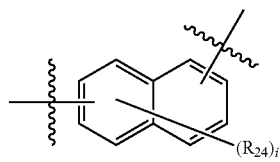

wherein d, e, f and g are each an integer ranging from 0 to 3, h and i are each an integer ranging from 0 to 6, $X_5$ to $X_7$ are each independently selected from the group consisting of CR'R", SiR'R", GeR'R", NR', PR', O, S and Se, $Y_1$ and $Y_2$ are each independently selected from the group consisting of CR', SiR', GeR', N and P, Z is selected from the group consisting of SiR'R", GeR'R", NR', O, S and Se, $R_5$ to $R_{24}$, R', R" and R'" are each independently selected from the group consisting of hydrogen; deuterium; a halogen group; a nitro group; a nitrile group; an imide group; an amide group —$CONX_1X_2$, wherein $X_1$ and $X_2$ may be the same or different and are each independently hydrogen, a substituted or unsubstituted $C_{1-25}$ alkyl group or a substituted or unsubstituted $C_{6-25}$ aryl group; a hydroxyl group; an ester group —$COOX_3$, wherein $X_3$ is a substituted or unsubstituted $C_{1-25}$ alkyl group or a substituted or unsubstituted $C_{6-25}$ aryl group; a carbonyl group —$COX_4$, wherein $X_4$ is a substituted or unsubstituted $C_{1-25}$ alkyl group or a substituted or unsubstituted $C_{6-25}$ aryl group; a substituted or unsubstituted $C_{1-25}$ alkyl group; a substituted or unsubstituted $C_{1-25}$ alkoxy group; a substituted or unsubstituted $C_{2-25}$ alkenyl group; a thiophene group unsubstituted or substituted with either a $C_{1-25}$ alkyl group or a $C_{1-25}$ alkoxy group; a selenophene group unsubstituted or substituted with either a $C_{1-25}$ alkyl group or a $C_{1-25}$ alkoxy group; a pyrrole group unsubstituted or substituted with either a $C_{1-25}$ alkyl group or a $C_{1-25}$ alkoxy group; a thiazole group unsubstituted or substituted with either a $C_{1-25}$ alkyl group or a $C_{1-25}$ alkoxy group; an arylamine group unsubstituted or substituted with either a $C_{1-25}$ alkyl group or a $C_{1-25}$ alkoxy group; and an aryl group unsubstituted or substituted with either a $C_{1-25}$ alkyl group or a $C_{1-25}$ alkoxy group;

a, b and c represent the mole fractions of the structures of chemical formulas 14 and 15, a is a real number in the range of $0<a\le 0.45$, b is a real number in the range of $0<b\le 0.45$, c is a real number in the range of $0.1\le c<1$, and $a+b+c=1$.

2. The random polymer of claim 1, wherein $R_3$ and $R_4$ are the same or different and are each independently hydrogen or a substituted or unsubstituted $C_{1-25}$ alkoxy group.

3. The random polymer of claim 1, wherein n is an integer ranging from 30 to 100.

4. The random polymer of claim 1, wherein the polymer has a molecular weight distribution of 1-100.

5. The random polymer of claim 1, wherein the polymer has a heteroaromatic group, an aromatic group or a halogen-substituted alkyl group as its end group.

6. The random polymer of claim 1, wherein chemical formula 1 is any one of the following structural formulas 1 to 14:

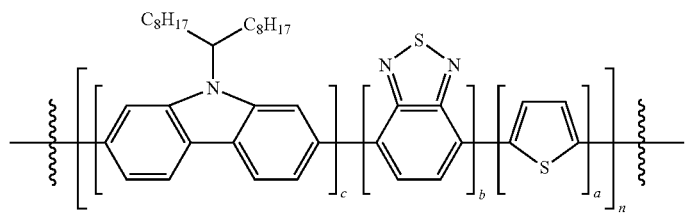

Structural formula 1

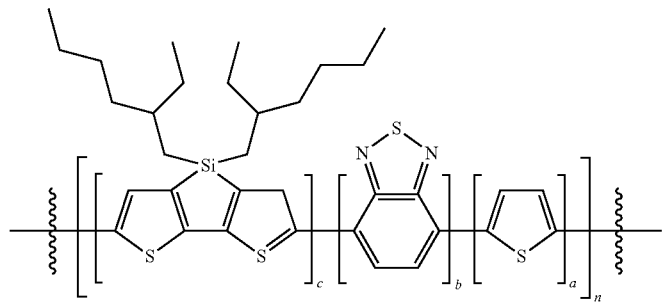

Structural Formula 2

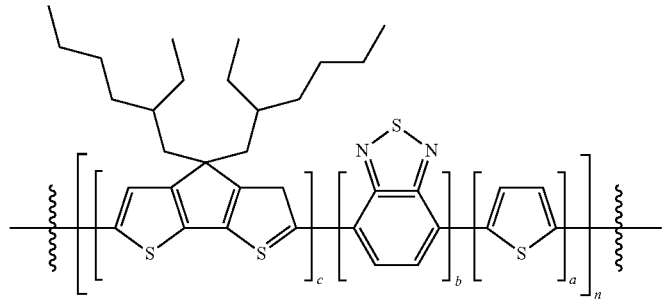

Structural Formula 3

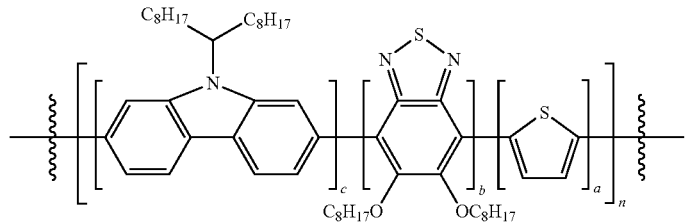

Structural Formula 4

-continued
Structural Formula 5
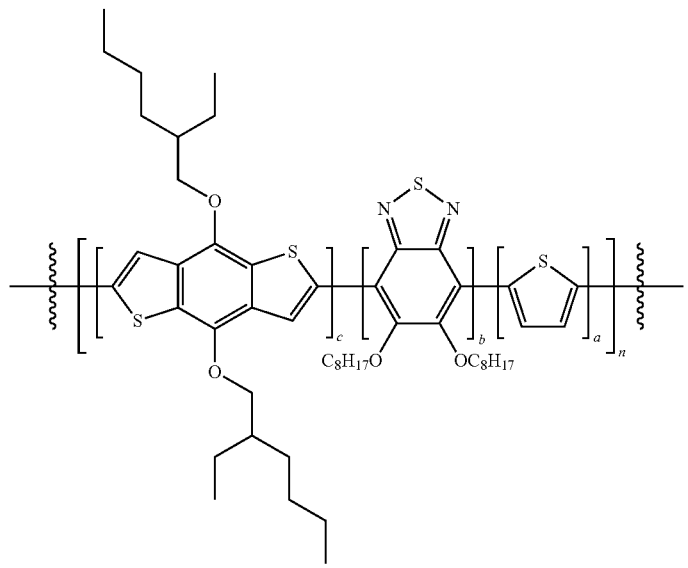
Structural Formula 6
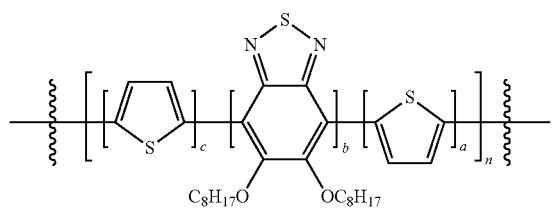
Structural Formula 7
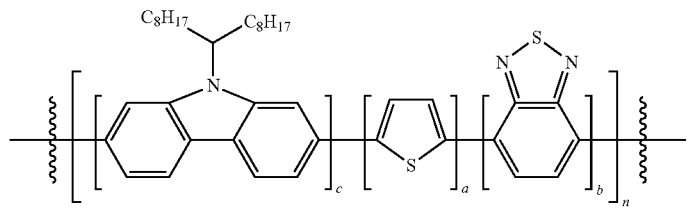
Structural Formula 8
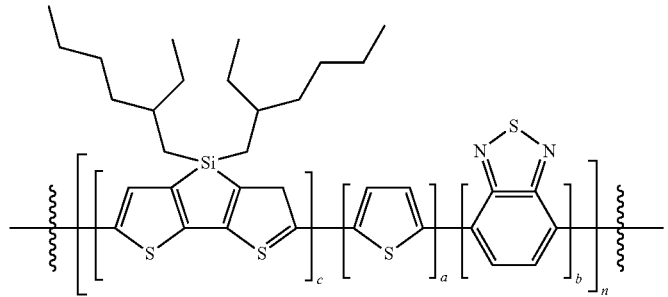
Structural Formula 9
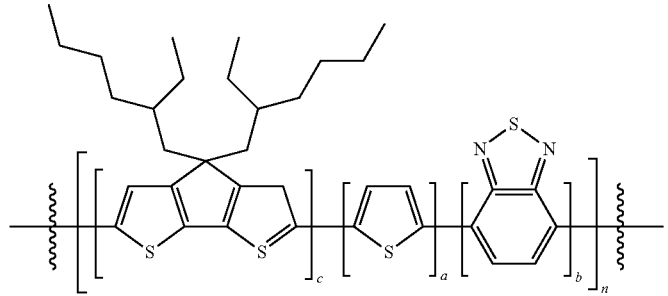

-continued
Structural Formula 10
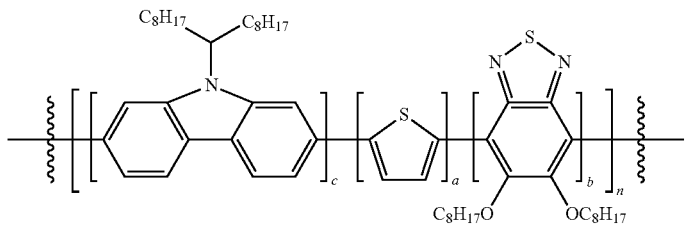
Structural Formula 11
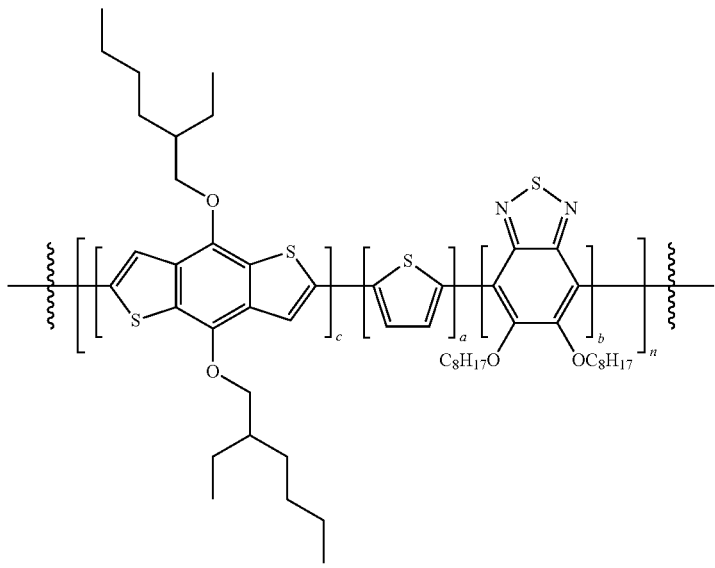
Structural Formula 12
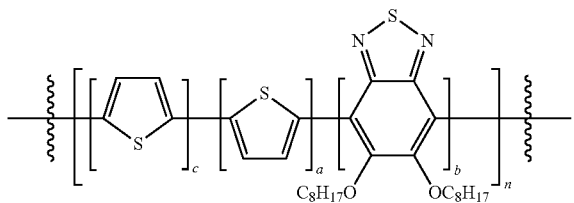
Structural Formula 13
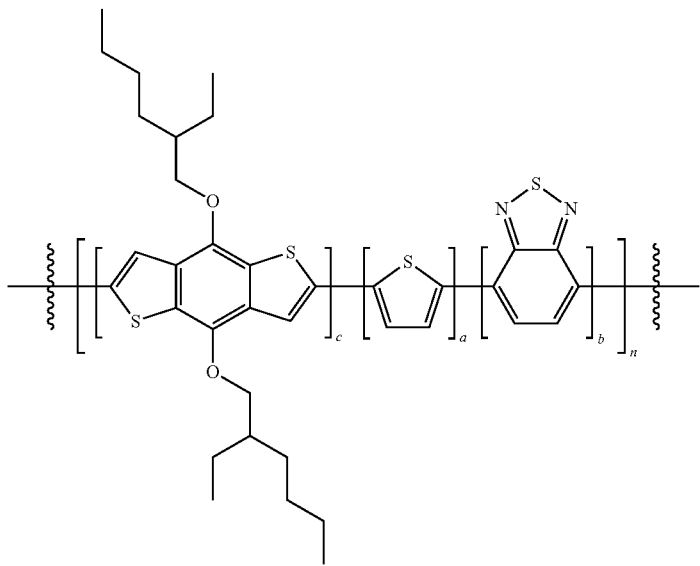

Structural Formula 14

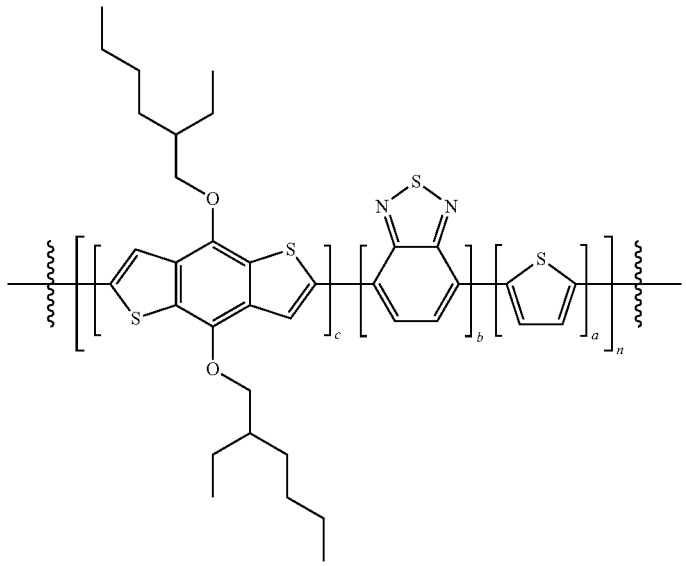

wherein a, b, c and n are as defined in chemical formulas 14 and 15.

7. An organic solar cell comprising a first electrode, a second electrode and one or more photoactive layers, wherein one or more of the photoactive layers comprises the random polymer of claim 1.

8. The organic solar cell of claim 7, wherein the photoactive layers comprise an electron donor material and an electron acceptor material.

9. The organic solar cell of claim 8, wherein the electrode donor material comprises the random polymer.

10. The organic solar cell of claim 8, wherein the electron acceptor material comprises one or more selected from the group consisting of fullerene, fullerene derivatives, vasocuproin, semiconductor elements, and semiconductor compounds.

11. The organic solar cell of claim 7, wherein the organic solar cell further comprises one or more of an electron transport layer and a hole transport layer.

12. The organic solar cell of claim 11, wherein one or more of the electron transport layer and the hole transport layer comprise the random polymer.

13. A method for fabricating an organic solar cell, the method comprising the steps of:
providing a substrate;
forming a first electrode on the substrate;
forming on the first electrode a photoactive layer comprising the random polymer of claim 1; and
forming a second electrode on the photoactive layer.

14. The method of claim 13, wherein the method further comprises, after the step of forming the first electrode, but before the step of forming the photoactive layer, a step of forming a hole transport layer on the first electrode.

* * * * *